United States Patent
Poulos

(10) Patent No.: US 9,326,801 B2
(45) Date of Patent: May 3, 2016

(54) FENESTRATED BONE SCREW AND METHOD OF INJECTING BONE CEMENT INTO BONE STRUCTURE

(71) Applicant: Nicholas Poulos, Belleville, IL (US)

(72) Inventor: Nicholas Poulos, Belleville, IL (US)

( * ) Notice: Subject to any disclaimer, the term of this patent is extended or adjusted under 35 U.S.C. 154(b) by 210 days.

(21) Appl. No.: 14/148,270

(22) Filed: Jan. 6, 2014

(65) Prior Publication Data

US 2014/0194886 A1 Jul. 10, 2014

Related U.S. Application Data

(60) Provisional application No. 61/750,131, filed on Jan. 8, 2013.

(51) Int. Cl.
| | | |
|---|---|---|
| *A61B 17/58* | (2006.01) | |
| *A61B 17/60* | (2006.01) | |
| *A61F 2/00* | (2006.01) | |
| *A61B 17/70* | (2006.01) | |
| *A61B 17/86* | (2006.01) | |
| *A61B 17/88* | (2006.01) | |

(52) U.S. Cl.
CPC ............ *A61B 17/7098* (2013.01); *A61B 17/864* (2013.01); *A61B 17/8822* (2013.01)

(58) Field of Classification Search
None
See application file for complete search history.

(56) References Cited

U.S. PATENT DOCUMENTS

| | | | |
|---|---|---|---|
| 4,484,570 A | 11/1984 | Sutter et al. | |
| 6,048,343 A | 4/2000 | Mathis et al. | |
| 6,517,542 B1 | 2/2003 | Papay et al. | |
| 6,565,572 B2 | 5/2003 | Chappius | |
| 6,755,835 B2 | 6/2004 | Schultheiss et al. | |
| 7,699,852 B2 | 4/2010 | Frankel et al. | |
| 8,747,411 B2* | 6/2014 | Mitchell ............ | A61B 17/7098 606/104 |
| 2004/0225292 A1* | 11/2004 | Sasso ................. | A61B 17/8615 606/916 |
| 2008/0234756 A1 | 9/2008 | Sutcliffle et al. | |

OTHER PUBLICATIONS

John C. Sutcliff, FRCS*, Farzam Vahzifehdan, MD, Marcus Richter, MD; Preliminary experience with the TangoRS; poryaxial, percutaneous, cement augmentation pedicle screw system. http://www.ispub.om/ostia/index.php?xm1FilePath=jounals/ijss/front.xml; 6 pages * The London Spine Clinic, 119 Harley Street London, England ** Spine Center, St. Josefs-Hospital, Solmsstrasse 15, 65189 Wiesbaden, German.

Lucas Amendola, Alessandro Gasbarrini, Matteo Fosco, Christiano Esteves Simoes, Silvia Terzi, Federico de Iure, Stefano Boriani Fenestrated pedicle screws for cement-augmented purchase in patients with bone softening: a review of 21 cases J. Orthopaed Traumatol (2011) 12:193-199 DOI 10,1007/s10195-011-0164-9.

(Continued)

*Primary Examiner* — Sameh Boles
(74) *Attorney, Agent, or Firm* — Polster, Lieder, Woodruff & Lucchesi LC

(57) ABSTRACT

A fenestrated bone screw and method of use is disclosed in which a bone cement injection tube may be readily and sealably connected to the head of the bone screw by means of a bayonet connector so that bone cement from a cement pump may be forced into a cannula of the bone screw and into the bone structure proximate the fenestrations of the bone screw. Upon completion of the injection of the bone cement, the cement tube may be readily disconnected from the bone screw in such manner that leakage of bone cement is minimized. A surgical method of injecting bone cement into bone structure using such a cannulated, fenestrated bone screw is also disclosed.

17 Claims, 15 Drawing Sheets

(56) References Cited

OTHER PUBLICATIONS

Medtronic Media Contacts: Jeff Warren, Investor Relations 763-505-2696;Victor Rocha, Public Relations, 901-399-2401 Medtronic Introducts the CD HORIZON® Fenestrated Screw Spinal System; News Release Jul. 1, 2011 10:54 AM ET; Memphis, Tenn.; 2 pages.
Spiros L Blackburn, M.D.*, Wilson Z. Ray, M.D.*, Neill Wright, M.D.* The use of fenestrated screw system with PMMA augmentation in osteoporotic bone Department of Neurosurgery, Washington University, St. Louis, MO; 11 pages; published before Jan. 6, 2012.
Viper Cortical Fix Fenestrated Screw, Surgical Technique & Product Catalogue, Guide for Open and MIS Procedures, DePuy Spine, Inc. 2011, 9085-38-000: Rev. 2 12/11, www.depuy.com; published before Jan. 6, 2012.
Surgical Technique; Pedestal™ Fenestrated Tap System, The Art & Science of Spine Surgery, Abbott Spine; 19 pages; published before Jan. 6, 2012.

* cited by examiner

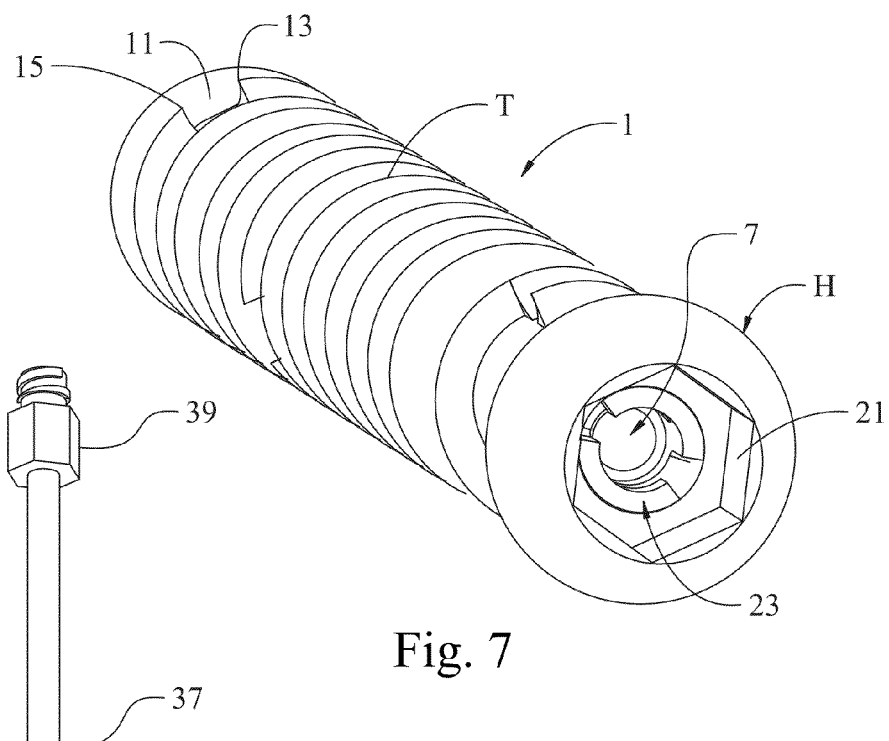
Fig. 7
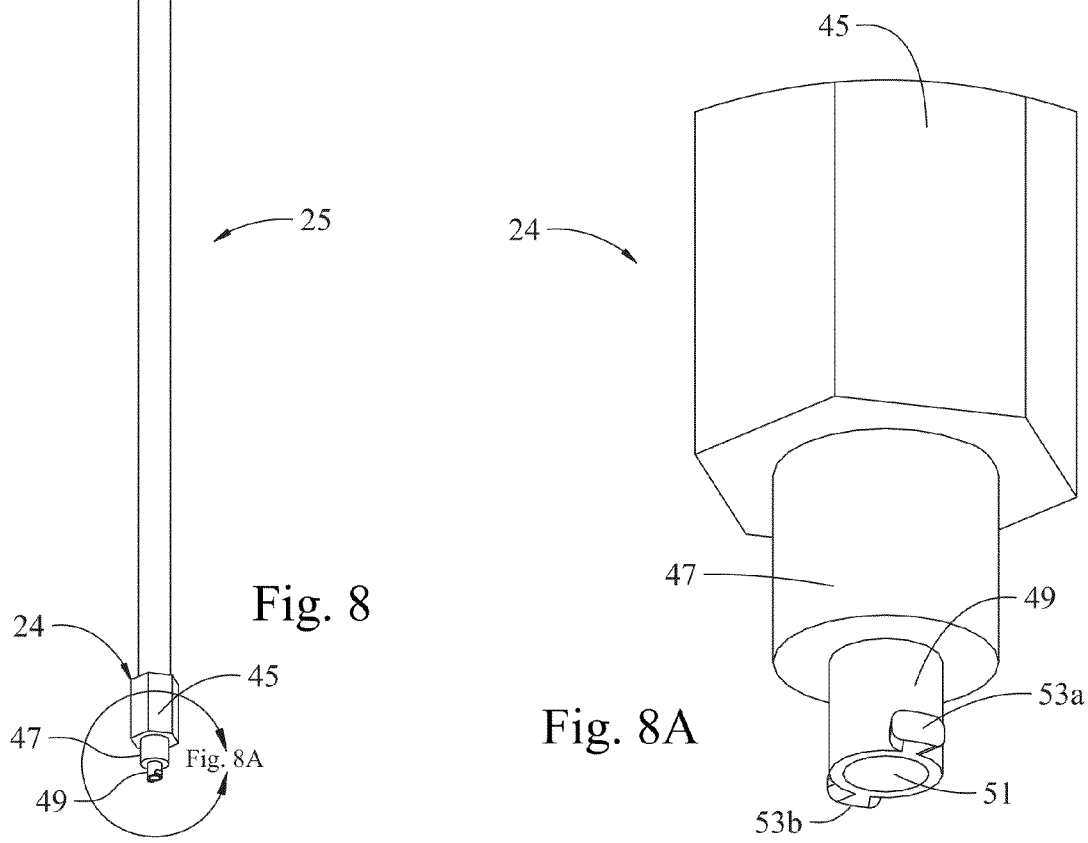
Fig. 8
Fig. 8A

ALIF

DLIF

TLIF

FENESTRATED BONE SCREW AND METHOD OF INJECTING BONE CEMENT INTO BONE STRUCTURE

CROSS-REFERENCE TO RELATED APPLICATIONS

This application claims priority to U.S. Provisional Patent Application No. 61/750,131, filed on Jan. 8, 2013, which is herein incorporated by reference in its entirety herein.

STATEMENT REGARDING FEDERALLY SPONSORED RESEARCH OR DEVELOPMENT

Not Applicable

BACKGROUND OF THE DISCLOSURE

This disclosure relates to fenestrated bone screws, and in particular to fenestrated pedicle bone screws, and to methods of installing such fenestrated bone screws in a variety of surgeries, particularly spine surgeries, and to the methods of injecting bone cement (e.g., polymethyl methacrylate (PMMA), or the like) into the proximate bone structure into which such fenestrated screws are installed.

In many instances, particularly in spine surgeries, the patient may have diminished or osteoporotic bone quality, which lessens the purchase of bone screws in such bone structure. In spine surgery, such diminished bone quality oftentimes precludes stabilization of the vertebrae and leads to pedicle screw loosening and pullout.

In order to enhance fixation of bone screws in osteoporotic bone, multiple solutions have been tried. Pedicle screw design has been optimized including greater thread depth, decreased thread cross-sectional thickness, buttress thread design, greater purchase length, and maximized major diameter. Greater insight into insertion technique by the surgeon has been achieved. Smaller diameter pilot holes, undertapping, and avoidance of multiple passes are standard technique as well as fixating more levels to distribute loads more widely. Pedicle screw surface coating with hydroxyapatite results in increased pullout resistance and decreased loosening by promoting bonding between bone and the apatite coating of the screw. Unfortunately these screws are expensive and suboptimally perform in biologically challenged osteoporotic bone.

Kyphoplasty augmented pedicle screw fixation represents an initial attempt at utilizing the injection of bone cement to increase pedicle screw pullout strength. Kyphoplasty is typically performed by the injection of 2-3 ml. of bone cement into a void in the bone structure formed by the inflation of a special balloon into the vertebrae. As the balloon inflates, it compacts the soft inner bone structure to create a void or cavity inside of the vertebrae. The balloon is then removed and bone cement is injected into the cavity. However, if such procedure is used to enhance the purchase of, for example, a pedicle screw to be inserted into the vertebrae, the screw must be inserted before the cement has hardened.

While screw loosening and the tendency of the screw to pull out of the bone are reduced, percutaneous screw placement is not possible and thus kyphoplasty cannot be used with minimal invasive surgery (MIS) platforms. Further, once the screw is placed, it cannot be repositioned if the screw is inserted along an unsatisfactory trajectory. Still further, if multi-level fixation is required, such kyphoplasty augmented screw placement would require multiple kyphoplasty kits (e.g., balloons and injection systems) that would make the procedure prohibitively expensive.

Further technological improvements have resulted in the development of various systems using cannulated/fenestrated bone screws for injecting bone cement into the bone structure into which the fenestrated bone screw has been inserted. Such cannulated/fenestrated screws typically have a central bore or cannula extending lengthwise of the screw along its central axis with the cannula extending through the tip of the screw. One or more side bores or fenestrations are typically located along the length of the bone screw in the area of the bone structure into which it is desired to inject the bone cement. The number of fenestrations may vary, but typically there may be between 3 and 6 fenestrations in the screw, depending on the length of the screw. Such screws are commercially available in various lengths and diameters.

In spine surgeries, such fenestrated bone screws may be used in either minimum invasive surgeries (MIS) or in open surgical procedures. The placement of the screws in the vertebrae or pedicles is carried out using known techniques for targeting and placement of the screws. A cement delivery cannula is connected to the cannulated screw. A cement pump is connected to the delivery cannula and the surgeon pumps bone cement (preferably a radio opaque cement) through the delivery cannula into the cannulated bone screw, out the fenestrations and the distal end of a fully cannulated screw into the surrounding bone structure before the cement has hardened. Fluoroscopy is used monitor the injection or extrusion of the cement into the bone structure. Once the cement has been injected into the bone structure, the delivery cannula is removed. Of course, once the cement has set up, enhanced screw purchase and stability of the bone structure results.

While such prior cannulated/fenestrated screw and cement injection systems have worked for their intended purpose, deficiencies have been found. The coupling and uncoupling of the cement injection system to the screw head of such screw bone cement augmentation systems has been problematic. Typically, the attachment of the cement injection cannula to the screw head has not been mechanically secure such that the surgeon oftentimes was required to hold the cement injection cannula docked to the screw head and to monitor for cement leakage Particularly in MIS procedures, the screw head is not visible to the surgeon such that it is difficult to reversibly mechanically connect the cement injection cannula to the screw head.

Still further, with such prior art cannulated/fenestrated screws, if the cannula fully extended to and through the tip of the screw, upon insertion of the screw into the bone structure, a bone core would enter the cannula of screw with final positioning of the screw in the desired anterior one third of the vertebral body. This bone core would block or occlude the flow of cement in the main channel of the screw and would block the flow of cement to the fenestrations or side bores effectively rendering the desired function useless. As a result, in such prior cannulated/fenestrated pedicle screws, the location of the injected bone cement is potentially along the posterior half of the screw in the posterior of the vertebrae, which is a far from optimal because of the potential extravasation of the bone cement into the spinal canal and foramen.

There are other prior systems where a cement delivery cannula is inserted into the axial bore or central cannula of the fenestrated screw. Of course, in order to enable the delivery cannula to be inserted into the central bore of the screw, there must be sufficient clearance between the inside diameter of the central bore of the screw and the outside diameter of the delivery cannula. Further, such cement delivery cannulas are typically elongate, small diameter tubes, which provide significant resistance to the flow of the cement for efficient injection of cement.

SUMMARY OF THE DISCLOSURE

A bone screw is disclosed having a shank, a tip, and a head. At least a portion of the shank has bone threads thereon for being threaded into bone structure. The shank has a longitudinal cannula therein. A plurality of fenestrations extends outwardly from the cannula to the exterior of the screw. The head of the screw has a central opening with the outer end of the central opening being configured to form a socket for receiving a driving tool for driving the screw into bone structure, and with the inner portion of the central opening being configured to form a connector so as to be sealably connected to a source of bone cement so that bone cement may be delivered to the cannula and forced out of the fenestrations and into bone structure proximate the fenestrations.

A method of injecting bone cement into surrounding bone structure is disclosed comprising the steps of installing a bone screw into bone structure. The bone screw has a shank, a tip, and a head. At least a portion of the shank has bone threads thereon. The shank has a cannula extending from the head along the central axis of the screw. A plurality of open fenestrations extends outwardly from the cannula. The head of the screw has a central opening with the inner portion of the central opening being in communication with the cannula and with the outer portion of the central opening configured to receive a driving tool for driving the screw into bone structure. The inner portion of the central opening is configured to be sealably coupled to and uncoupled from a supply of bone cement so that bone cement may be delivered to the cannula and forced out of the fenestrations into the bone structure adjacent the fenestrations. The method further includes sealably connecting the supply of bone cement to the screw, and injecting bone cement into the cannula of the bone screw and into the bone structure proximate the fenestrations.

Another method of the present disclosure for injecting bone cement into bone structure comprises the steps of installing a bone screw into bone structure. The bone screw has a shank, a tip, and a head, and at least a portion of the shank has bone threads thereon. The shank has a cannula extending along the central axis of the screw, and a plurality of open fenestrations extending outwardly from the cannula. The head has a central opening with the outer end portion of the opening is configured to receive a driving tool for driving the screw into bone structure. The central opening has a female connector positioned therein for releasably, sealably receiving a cement injection tube so that a suitable bone cement may be forcibly injected into the cannula of the screw and forced out of the fenestrations and into the surrounding bone structure. The method further involves sealably connecting the cement injection tube to the screw, and connecting a cement pump to the cement injection tube. Then, cement is injected into the cannula of the bone screw and into the bone structure proximate the fenestrations.

Still another method is disclosed for injecting bone cement into surrounding bone structure comprises installing a plurality of bone screws into bone structure, such as adjacent vertebrae bodies. Each of the bone screws has a shank, a tip, and a head with at least a portion of the shank having bone threads thereon, with the shank having a cannula extending along the central axis of the screw, and with a plurality of open fenestrations extending from the cannula. The head of the screw has a central opening with the outer end of the central opening being configured to receive a driving tool for driving the screw into bone structure, and with the inner end of the central opening being configured to sealably receive a cement delivery tube so that a suitable bone cement may be forcibly injected into the cannula of the screw and forced out of the fenestrations and into the surrounding bone structure. The method further comprises the following steps: sealably connecting a cement delivery tube to each the screws; connecting a cement pump to a first one of the cement injection tubes; injecting cement into the cannula of first one the bone screws and into the bone structure proximate the fenestrations of the first bone screw; removing the cement pump from the first cement injection tube substantially without leakage of cement adjacent the head of the screw; connecting the cement pump to a second cement injection tube; injecting cement into the cannula of a second of the bone screws; and removing the cement injection tube from the second screw substantially without leakage of cement adjacent the head of the screw.

The cannulated bone screws and methods of the present disclosure are intended to overcome the above-mentioned problems of prior bone screws and bone cement injection methods or procedures. Other objects and features will be in part apparent to those of ordinary skill in the art and will be in part pointed out in in the description of the preferred embodiments.

BRIEF DESCRIPTION OF THE DRAWINGS

FIG. 7 is a view similar to FIG. 6 with the cement delivery collar installed in the bore;

FIG. 8 illustrates a cement delivery tube of the present disclosure having a quick attachment/quick release bayonet connector on its distal end for the sealable attachment of the delivery tube to the cement delivery collar and to the head of a fenestrated, cannulated screw (as shown in FIGS. 9-10A) and for the ready removal of the tube;

FIG. 8A illustrates the distal end of the cement delivery tube shown in FIG. 8 on an enlarged scale having a male bayonet connector configured to mate with the female cement delivery collar installed in the head of the screw, as shown in FIG. 7, so that upon insertion of the male connector into the center opening of the delivery collar and upon twisting the tube through a fraction of a turn, the cement delivery tube is mechanically and sealably connected to the bone screw such that upon the injection of bone cement, leakage of the bone cement at the junction of the cement delivery tube and the screw such that the chance of extravasation of the cement into the surrounding wound is minimized;

FIG. 12 illustrates the insertion of a Jamshidi needle and trocar into the bone structure, for example lumbar vertebrae L4, which is desired to be reinforced with bone cement;

FIG. 13 illustrates a Jamshidi needle, as shown in FIG. 12, at the desired location for the installation of a fenestrated pedicle screw, where a sharp guide wire is inserted through the Jamshidi needle to aid in the installation of a fenestrated cannulated screw of the present disclosure;

FIG. 14 illustrates the installation of sequential dilation tubes over the guide wire, as shown in FIG. 13, for dilation of the fascia and muscles;

FIG. 15 illustrates the establishment of a surgical corridor through the largest diameter dilator tube with the guide wire extending through and from the distal end of the dilator tube;

FIG. 16 illustrates the creation of a pilot hole in the pedicle of a vertebrae body (e.g., L4) using a cannulated tap passed over the guide wire;

FIG. 17 illustrates a screw extender for initial cannulated fenestrated screw placement over a guide wire;

FIG. 18 illustrates a tool or screw driver extender of the present disclosure for engaging the socket of a bone screw of the present disclosure for driving the screw into bone structure after the guide wire has been withdrawn, the screw driver having an extension rod that is received in the central bore or cannula of a cannulated bone screw of the present disclosure so as to prevent the cannula and the fenestrations of the screw from being occluded with bone material upon driving the bone screw into bone structure;

FIG. 19 illustrates the final positioning of a fenestrated/cannulated pedicle screw of the present disclosure using a screw driver extender, as shown in FIG. 18;

FIG. 20 is an enlarged view of FIG. 19 with the cortical bone removed illustrating the final desired position of a fully cannulated fenestrated pedicle screw of the present disclosure installed using a screw driver of the present disclosure with the extension rod of the screw driver extending substantially the full length of the cannula so as to prevent bone core material from occluding the cannula and the fenestrations, with the length of the extension rod being sized relative to the screw such that the end of the rod preferably does not protrude beyond the end of the screw;

FIG. 21 is a diagrammatic illustration of a cement delivery tube, as illustrated in FIGS. 8-10A, ready to be mechanically and sealably coupled to a cannulated/fenestrated screw of the present disclosure that has been installed in a vertebrae, the coupling being accomplished by a reversible bayonet connector of the present disclosure for sealably connecting the cement delivery tube to the head of the screw and for the delivery (injection) of bone cement under pressure into the fenestrated screw of the present disclosure and for injection of the bone cement into the bone structure adjacent the fenestrations in the screw without leakage of the bone cement from the connection of the cement tube to the head of the screw;

FIG. 22 illustrates the attachment of a cement pump to the cement delivery tube for the forcible injection of bone cement through a cannulated/fenestrated screw of the present disclosure and into the bone structure adjacent the fenestrations of the bone screw;

FIG. 23 illustrates the connection of the cement delivery tube to the head of a bone screw in accordance with the present disclosure;

FIG. 24 illustrates the forcible injection of bone cement into the bone structure proximate the fenestrations and proximate the tip of a fully cannulated pedicle screw of the present disclosure, however it will be understood that this view would be substantially the same if a blind end cannulated screw is employed except that cement would not be injected into the bone structure proximate the tip of the blind end screw;

FIG. 25 illustrates a plunger inserted into the cannula of a fully cannulated bone screw upon completion of the injection of cement into the bone screw and into the surrounding bone structure for clearing residual cement from the central bore or cannula of the bone screw;

FIG. 26 illustrates the technique of the present disclosure for multi-level vertebrae fixation using an open surgical procedure with either fully cannulated or blind-end cannulated fenestrated pedicle screws of the present disclosure and injecting bone cement into the bone structure adjacent the fenestrations of the bone screws.

Corresponding reference characters indicate corresponding structure and features throughout the several views of the drawings.

DESCRIPTION OF PREFERRED EMBODIMENTS

Figure 1:
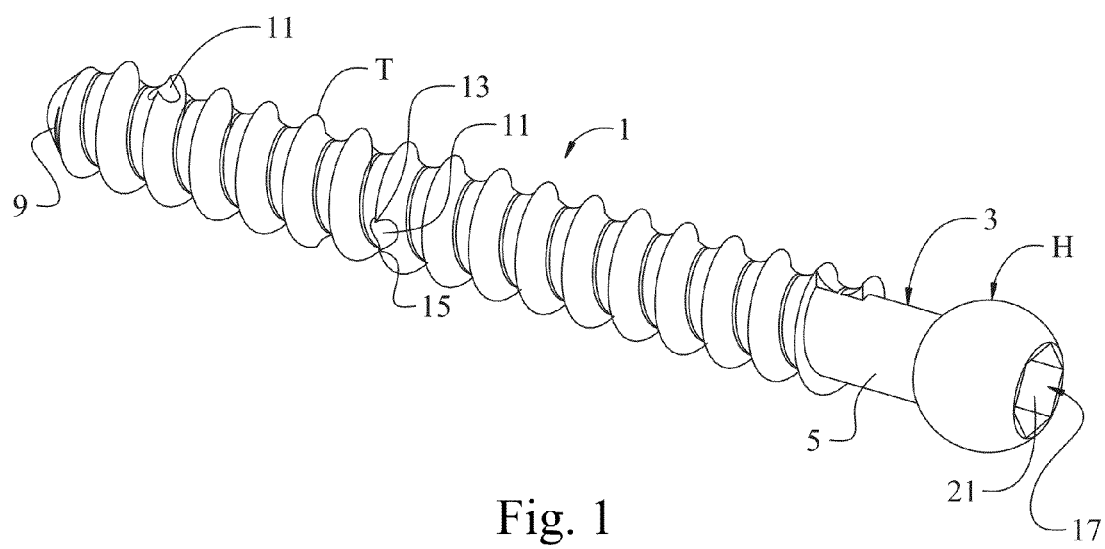
FIG. 1 is a perspective view of a cannulated/fenestrated pedicle screw of the present disclosure.

Referring now to FIG. 1, a fenestrated/cannulated bone screw of the present disclosure, and more particularly a pedicle screw, is illustrated in its entirety by reference character 1. Screw 1 has a part-spherical head H for the attachment of a poly-axial saddle (not shown) that is conventionally used in spinal surgery. However, those skilled in the art will recognize that heads H of different designs, shapes, and purposes may be used in conjunction with the screw of the present disclosure. Screw 1 has a shank, as generally indicated at 3, having bone threads T formed or machined on a substantial length of the shank. As indicated at 5, the portion of the shank proximate head H may be free of threads T, however, the threads may extend proximate the head H.

Figure 2:
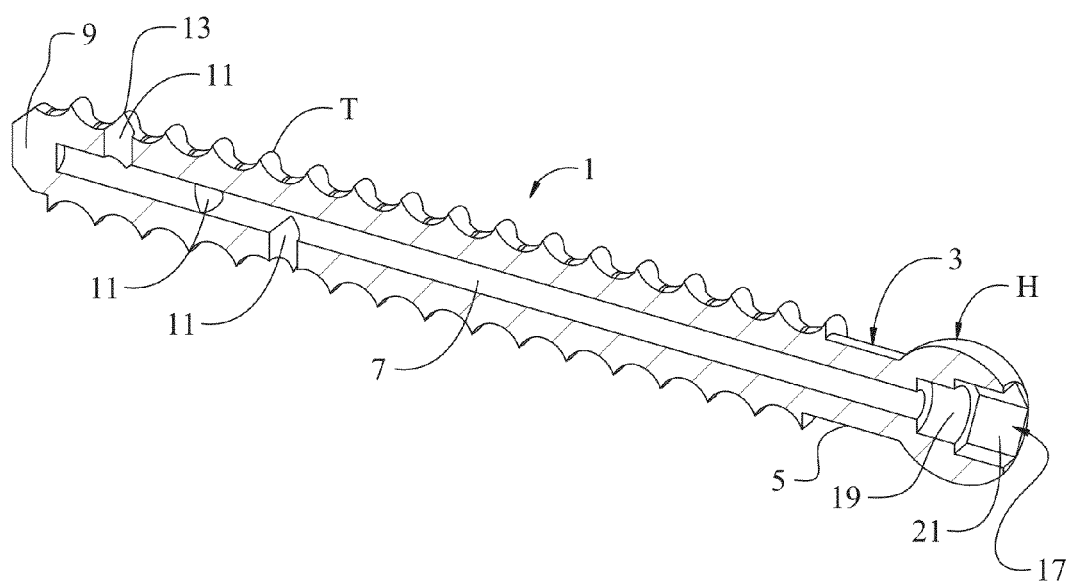
FIG. 2 is a longitudinal cross sectional view of a blind end cannulated/fenestrated pedicle screw of the present disclosure illustrating a blind central bore or cannula extending from the head of the screw toward the distal end of the screw and illustrating a plurality of side bores or fenestrations extending from the central bore with each of the fenestrations preferably, but necessarily, intersecting a respective thread crest.
Figure 3:
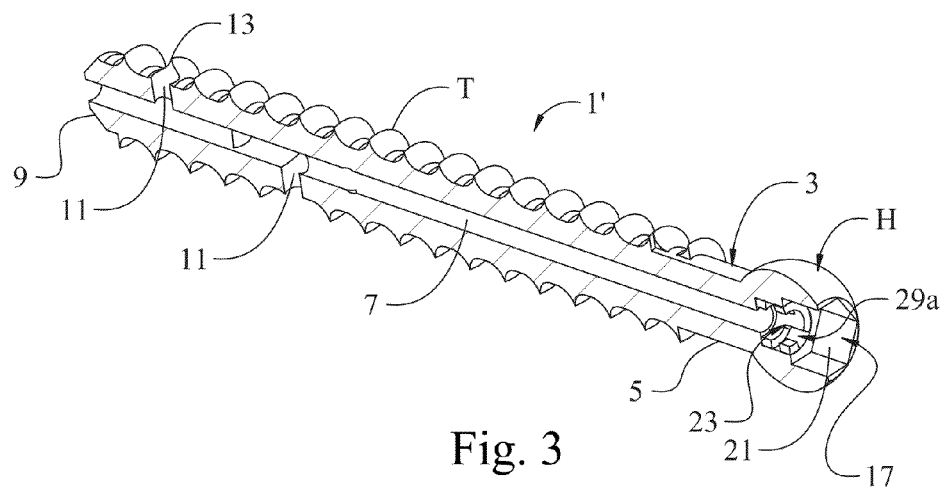
FIG. 3 is longitudinal cross section of a fully cannulated/fenestrated pedicle screw of the present disclosure similar to the above-described blind end cannulated/fenestrated pedicle screw, as shown in FIG. 2, except the central bore or cannula extends out through the end or tip of the screw.

More particularly, screw 1, as shown in FIG. 2, is a blind end cannulated screw having a cannula 7 extending from head H to the distal end of the screw, but where the cannula 7 does not extend through the tip 9 of the screw. The term "cannula" means any longitudinal bore that extends lengthwise of the screw. A plurality of fenestrations or side bores 11 extend preferably from the crest of a thread T to the cannula 7. The term "fenestration" means any type of an opening, side bore or aperture leading from the cannula to the exterior of the screw. It will be appreciated that the number of fenestrations can vary, depending on the application for the screw. For example, 3-6 fenestrations may be provided in a typical pedicle bone screw of the present disclosure. The fenestrations 11 are longitudinally spaced along the cannula and are radially spaced from one another so as to generally enable the uniform injection of bone cement into the bone structure in which the screw is installed. FIG. 3 illustrates a fully cannulated screw 1' having its cannula 7 extending from the head H through the tip 9 of the screw. Again, a plurality of fenestrations 11 is provided and, preferably, but not necessarily, such fenestrations extend from the crest of a thread to the cannula 7, and not to the root of the thread. The fenestrations may be located at different radial and longitudinal positions relative to the shank of the screw so that the bone cement may be injected into bone structure around and along the length of the screw in proximity to the fenestrations for reinforcement of the bone structure. For example, the diameter of the cannula 7 in both screws 1 and 1' may preferably be about 1.6 mm. (or larger) and the diameter of the fenestrations may also be about 1.6 mm. so as to insure that the bone cement flows through the fenestrations instead of taking the path of least resistance and flowing out of the time of the screw for fully cannulated screws 1'. A diameter of about 1.6 mm. of the cannula 7 has been found to be the smallest practical diameter for vertebroplasty applications. However, other diameters of cannula 7 and fenestrations 11 may be used in accord with this disclosure.

As shown in FIG. 1, by positioning fenestrations 11 so that they exit the threads at the crest of a thread, the outlet end of each of the fenestrations has a leading edge 13 relative to the direction of rotation of the screw upon insertion of the screw and a trailing edge 15 on the opposite side of the fenestration so that the leading and trailing edges protect the fenestration and minimize occluding of the fenestrations with bone material as the screw is threaded into the surrounding bone structure. Of course, with the fenestrations being substantially free of occluding bone material, the injection of bone cement into the surrounding bond structure is enhanced.

Figure 4:
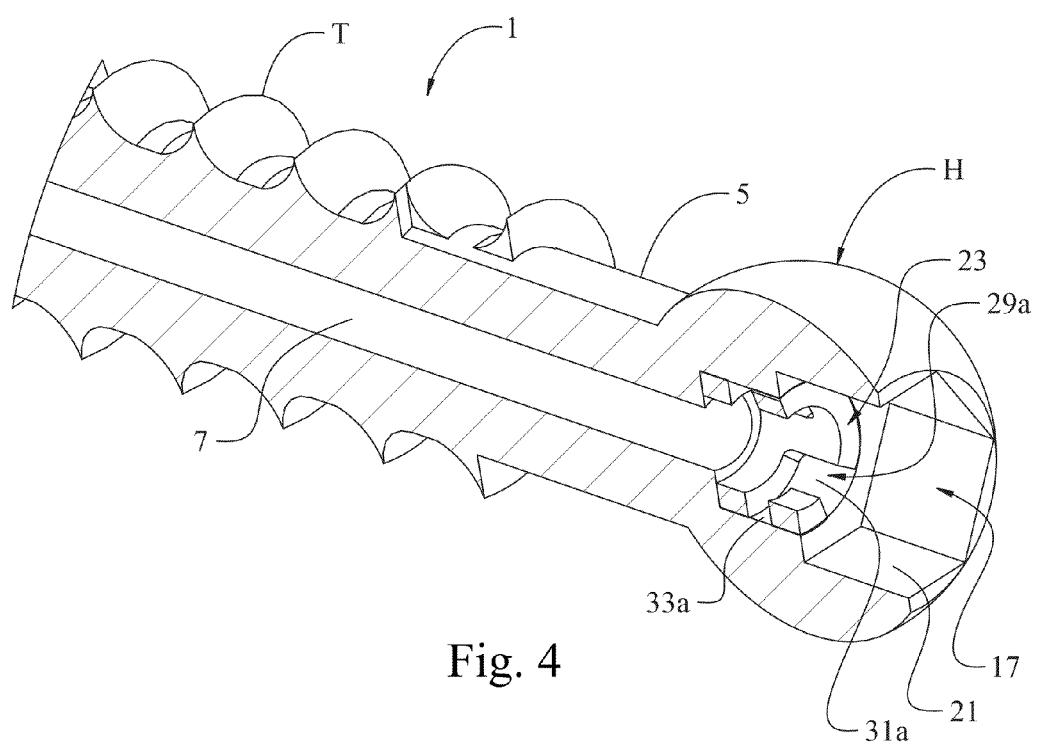
FIG. 4 is perspective cross sectional view on an enlarged scale of the head and the proximate portion of a cannulated/fenestrated screw of the present disclosure having a socket formed in the head for receiving a screw driving tool and a cement delivery collar of the present disclosure positioned inwardly of the socket for the ready and sealable attachment of a cement delivery or injection tube to the bone screw (shown in FIGS. 9-10A) for the ready installation and removal of the cement delivery relative to the screw.

As shown in FIGS. 3 and 4, the screw head H has an internal opening, as generally indicated at 17, formed therein having an inner cylindrical bore 19 and an outer screw driving socket 21 at the proximate end of the screw for receiving a complimentary screw driving tool. As shown in FIGS. 3 and 4, the screw driving socket 21 is in the shape of a hexagonal socket for receiving a hexagonal screw driving tool, but those skilled in the art will understand that any shape screw driving socket, such as a star-shaped or a Torq socket, may be employed.

As shown in FIGS. 3 and 4, a female bayonet connection collar or connector, as generally indicated at 23, is preferably installed within the cylindrical inner bore 19 of the screw head H. Collar 23 preferably permanently installed in bore 19 by being press fit or thermally shrunk into bore 19, or, more preferably, collar 23 may be adhesively secured within bore 19 by means of a suitable adhesive, such as Locktite® 601, commercially available from Henkel Corporation of Westlake, Ohio. While collar or connector 23 is shown to be a piece separate from the screw, those skilled in the art will recognized that the screw may be formed or cast with such a collar integral with the screw.

Collar 23 is preferably shown to be in the form of a hollow female tube-like bayonet connector that allows a male bayonet connector 24 carried by a cement dispensing tube 25, as shown in FIG. 8, to be readily inserted into a central bore 27 of collar 23 and to be sealably and securely connected to the collar and to be readily removed from the collar. With such a bayonet connection of the cement tube 25 to the head H of screw 1 using the bayonet connector 23, a surgeon need not be able to see the head H of the screw or the distal end of tube 25 to connect the tube to the screw. Moreover, as will be described herein, using such a bayonet connection, there is a tactile indication to the surgeon when the tube 25 is mechanically and sealably connected to the screw. This allows for the "blind" connection and removal (that is, the connection need not be within the field of view of the surgeon) of the cement tube 25 to screws 1 or 1', which is particularly important in performing percutaneous MIS spine surgical procedures. As shown in FIGS. 8, and 9-10A, tube 25 is shown to be a rigid tube, however, those skilled in the art will recognize that the tube may be constructed of a flexible material.

Figure 5:
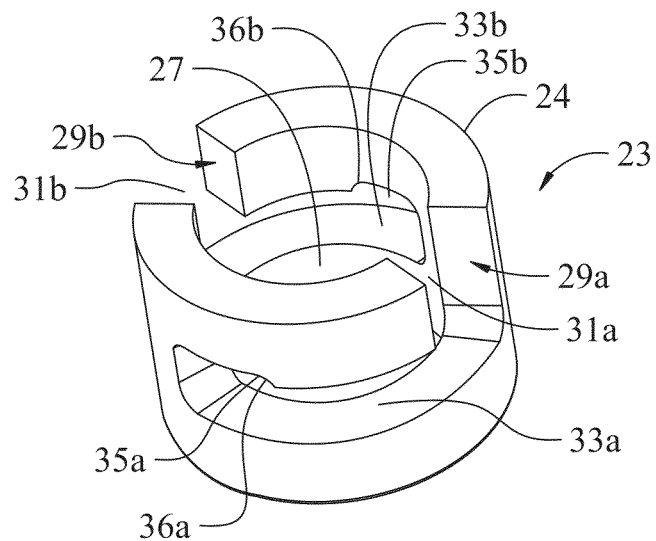
FIG. 5 is an enlarged perspective view of the cement delivery collar or connector illustrated in FIG. 4.
Figure 6:
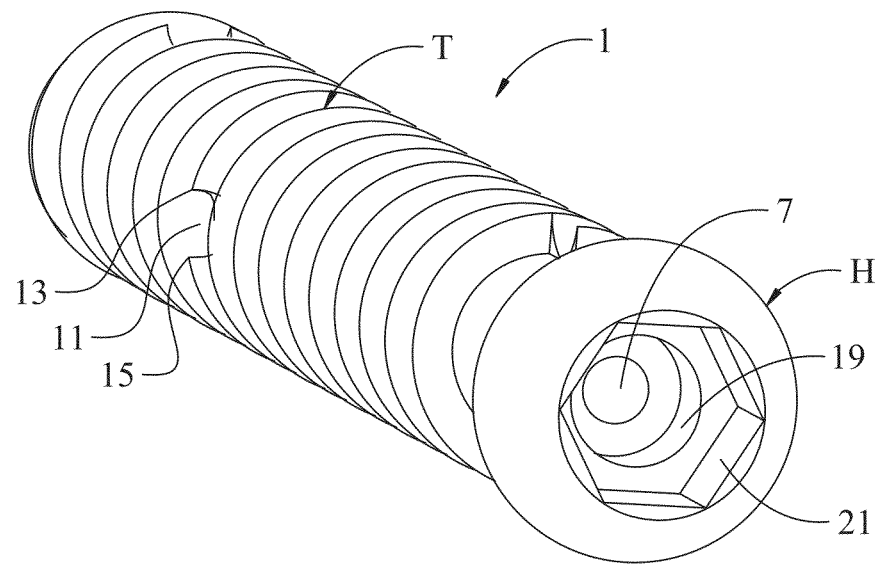
FIG. 6 is a perspective view of the head of a screw shown in FIGS. 1-4 prior to installation of the cement delivery collar or connector illustrating the socket and a recess or bore located inwardly of the socket surrounding the central bore or cannula of the screw for receiving the cement delivery collar.

The female bayonet connector collar 23 is shown in FIG. 5 to comprise a cylindrical hollow body 24 having a pair of diametrically opposed bayonet connection L-shaped slots, each of which is generally indicated at 29a, 29b. Because slots 29a, 29b are identical, only the slot 29a shown in the foreground of FIG. 5 will be described in detail. Slot 29a comprises a blind axial slot 31a extending from the proximate end of collar 23 when the collar is inserted in the central bore 19 of screw 1 toward the distal end of the screw. At the bottom or distal end of blind slot 31a, a circumferential slot 33a extends laterally or circumferentially from the blind slot through an arc of about 90°+about 30° or so. Near the end of slot 33a, a detent 35a is provided in the proximal outer surface of the circumferential slot for purposes as will appear. As shown, detent 35a has a sloped cam surface 36a for purposes as will appear.

Figure 11:
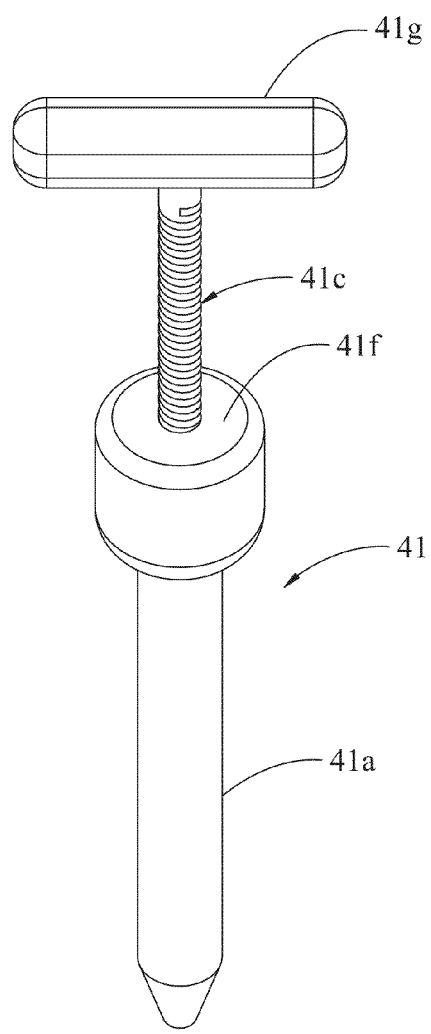
FIGS. 11 and 11A illustrate a conventional cement injection pump that may be used to supply cement under pressure to the cement delivery tube shown in FIGS. 8-10A so as to the inject the cement into the bone structure proximate the fenestrations in a bone screw of the present disclosure installed in bone structure, such as a vertebrae body.
Figure 11A:
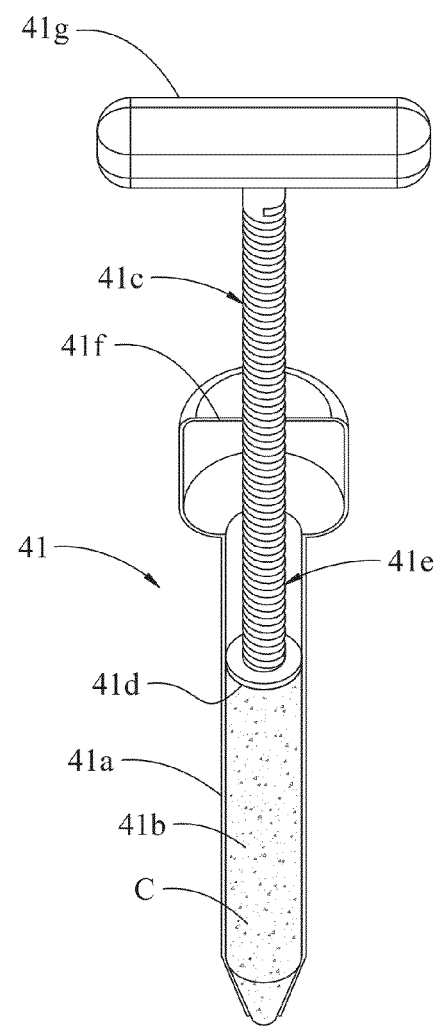

Referring now to FIGS. 8-10A, cement dispensing tube (also referred to as a cement injection tube) 25 is shown to have an elongate stem or tube 37 extending from a connector fitting 39 at its proximate end that allows the tube 37 to be connected to a suitable supply of bone cement, such as a bone cement pump or injector, as indicated in its entirety at 41 in FIGS. 11 and 11A. As heretofore mentioned, tube 37 may be of a suitable flexible or bendable material. A male bayonet connector, as generally indicated at 24, is provided on the distal end of tube 37 for the ready, positive sealable connection of the cement dispensing tube 25 to the female bayonet connector 23 installed in the head H of a screw 1 or 1' of the present disclosure, and for the ready removal of the cement dispensing tube from the screw by the surgeon.

Figures 9, 10, 10A:
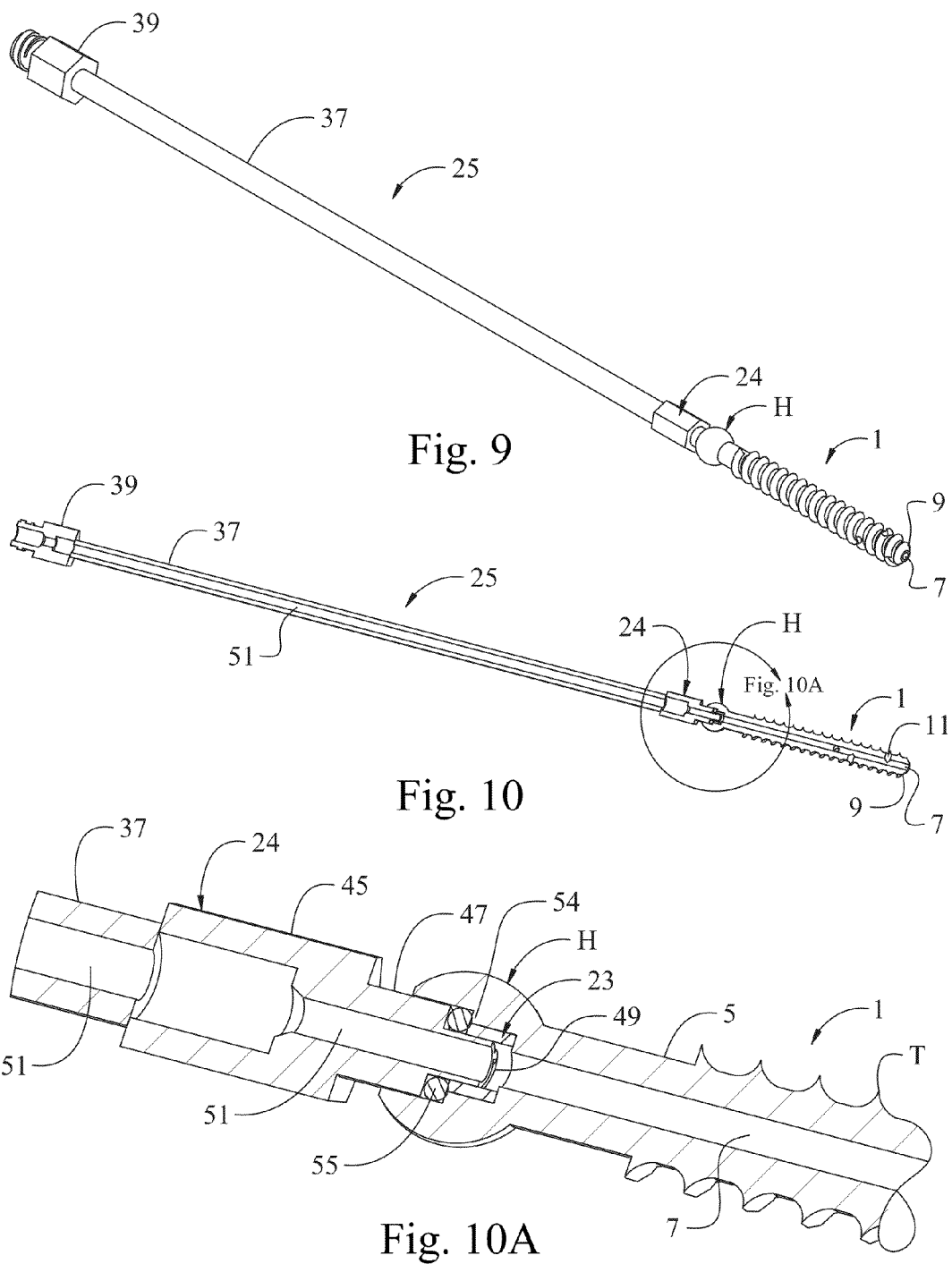
FIG. 9 is a perspective view of the cement delivery tube with its male bayonet connector sealably coupled to the cement delivery collar of a screw of the present disclosure.
FIG. 10 is a longitudinal cross sectional view of the cement tube and screw shown in FIG. 9.
FIG. 10A is a longitudinal cross sectional view of the distal end portion of the cement delivery tube and the head of the screw on an enlarged scale with the male bayonet connector inserted into and coupled to the female bayonet cement delivery collar of a screw of the present disclosure, and illustrating the provision of a seal, preferably an O-ring seal, to prevent the leakage of cement from the head of the screw upon injecting bone cement into the screw and for minimizing the chance of extravasation of the cement into the surrounding wound.

Specifically, male bayonet connector 24, as best shown in FIG. 8A, has a fitting body 45 that is sealably connected to the distal end of tube 37. Body 45 has a central hub 47 and a smaller diameter hub 49 extending generally axially from the distal end of fitting body 45, with hub 49 constituting a male bayonet connector adapted to be inserted into the central opening 27 and to be cooperable with the female bayonet connector 23 installed in the head H of a screw 1 or 1'. A central bore 51 (as best shown in FIGS. 10 and 10A) extends through fitting 34, tube 37, connector 45, central hub 47, and through distal hub 49 for the flow of a suitable bone cement from the cement pump or injector 41, through tube 37 and into the central bore or cannula 7 of screw 1.

A pair of diametrically opposed radially extending tangs 53a, 53b (as best shown in FIG. 8A) is provided on distal hub 49 with each tang disposed to be received by a respective bayonet slot 29a, 29b in collar 23. As shown in FIG. 10A, a shoulder 54 is present within opening 17 in the head H of the screw proximate the outer end of collar 23. A seal (preferably a compressible O-ring) 55 of a suitable elastomeric material or the like is held captive on hub 49 between tangs 53a, 53b and the larger diameter hub 47 for sealingly mating with shoulder 54 (as shown in FIG. 10A) within head H of the screw for establishing a sealable connection between tube 25 and the head H of screw 1 or 1'.

It will be appreciated that in order to connect cement dispensing tube 25 to a screw 1 or 1', as illustrated in FIGS. 21 and 23-26, the distal end of tube 25 is inserted into the surgical corridor, which may be established with dilator tubes as will be hereinafter described, so that the male bayonet connector 24 is generally aligned with the head of the screw that has been previously threadably inserted in the desired bone structure, such as a vertebral body. The surgeon then gently pushes the tube toward the screw rotates the tube so as to align tangs 53a, 53b with their respective axial blind slots 31a, 31b in collar 23. The surgeon will feel when the tangs are in register with their respective axial slots, and then the surgeon can continue to gently push the tube toward the screw until the tangs contact the bottom of their blind axial slots, at which point the tangs will be aligned with their respective circumferential slots 33a, 33b. The surgeon can readily feel when the tangs have reached the bottom ends of the axial blind slots 31a, 31b and are in alignment with the circumferential slots 33a, 33b in connector 23 even if the surgeon cannot visually see the end of the connector fitting 24 or the head H of the screw. Then, the surgeon twists or rotates the tube in one direction or the other (e.g., in clock-wise direction for the collar 23 shown in FIG. 5) so that the tangs enter the lateral or circumferential slots 33a, 33b and so that the tangs will move circumferentially until the tangs contact the ends of the slots 33a, 33b. As the tangs are moved to the bottom of blind axial slots 31a, 31b, the O-ring 55 is compressed between the distal end of hub 47 and shoulder 54 so as to seal the cement tube 25 relative to screw. It will be understood that the compressed O-ring thus also serves as a spring that resiliently biases the connector 24 away from collar 23 such that when the tangs enter detents 35a, 35b of connector 23, the tangs and the connector 24 will move axially outwardly away from the screw due to the bias of the compressed O-ring, but where the O-ring maintains a sufficient axial biasing force when tangs 53a, 53b are received in their respective detents 35a, 35b so as to insure that the cement tube remains connected and sealed to screw 1. As the tangs move into the detents, the surgeon will have a tactile indication that the tube 25 is mechanically locked and sealed relative to the screw so as to minimize an unintended uncoupling of the tube from the screw with possible leakage of cement deep in the wound site. The detents prevent the connector 24 from becoming accidentally dislodged or uncoupled from the collar 23. Further, the tube 25 remains positively and sealably connected to the screw head H while cement is injected under pressure from the cement pump 41, through tube 37, through male connector 24, through the central bore or cannula 7 of screw 1 and is forced under pressure out the fenestrations 11 and into the surrounding bone structure. Because the cement tube is positively, mechanically connected to the screw by means of tangs 53a, 53b being seated in detents 35a, 35b, and because the O-ring 55 is at least partially compressed between the distal end of hub 47 and shoulder 54, leakage of cement from the head H of the screw into the surrounding wound site is effectively prevented or minimized while the cement is injected into the bone structure surrounding the screw.

Upon the completion of the injection of cement into the bone structure surrounding a fenestrated screw 1 or 1' of the present disclosure, the tube 25 may be readily removed from the screw merely by pushing the tube toward screw 1 so that the tangs 53a, 53a move slightly toward the screw and by simultaneously twisting the tube in the opposite direction than it was installed (that is, in counter-clockwise direction for a connector 23, as shown in FIG. 5) until the tangs contact the sloped cam surfaces 36a, 36b of detents 35a, 35b. These cam surfaces cammingly move tangs toward screw 1 and thus allow the tangs to move clear of detents 35a, 35b and to thus permit the tangs to move into their respective circumferential slots 33a, 33b. It will be appreciated that as the surgeon begins to rotate the tube to disconnect the tube from the screw that it may be desirable that the surgeon pushes the tube toward the screw so as to somewhat compress O-ring 55 so as to make it easier for the tangs to move out of the detents 35a, 35b. Further rotation of the tube moves the tangs toward their respective axial slots 31a, 31b. When the surgeon cannot further rotate the tube because the tangs 53a, 53b have moved against the side of their respective axial slots 31a, 31b opposite the openings to circumferential slots 33a, 33b, the surgeon may axially withdraw the tube from the screw.

Referring now to FIGS. 11 and 11A, a source of a suitable bone cement is connected to cement delivery tube 25 so that the cement may be delivered to screw 1 or 1' under sufficient pressure to force the cement through cannula 7, through the fenestrations 11, and into the surrounding bone structure. One embodiment of this source of bone cement is shown to be a manually operated cement pump, indicated in its entirety at 41, is shown for being connected to the distal end of cement tube 25 so as to inject a suitable bone cement (e.g., polymethyl methacrylate (PMMA)) through the cannula 7 and the fenestrations 11 of a screw 1 or 1' into the bone structure surrounding the screw. As shown, pump 41 has a body 41a having a cylindrical cement reservoir 41b in which a quantity of a suitable bone cement C is contained. The pump 41 further has a plunger 41c having a piston 41d on its distal end. A threaded piston rod 41e and threadably engages a cap 41f affixed to the distal end of the body 41a. The piston rod extends axially out of the reservoir and it has a handle 41g that allows a surgeon to rotate piston rod 41e which in turn advances piston 41d so as to force bone cement C into tube 25, through the cannula 7 of the screw 1 or 1', and out of the fenestrations 11 so as to inject the bone cement into the bone structure surrounding the screw.

While not shown in FIGS. 11, 11A, it will be understood that a suitable fitting or attachment is provided on the distal end of body 41a so that the pump may be connected to the connector 39 of cement injection tube 25. Further, a flexible hose (also not shown) may be used to couple pump 41 to tube 25, or the tube may be of flexible material. Those skilled in the art will recognize that any suitable bone cement pump may be used in accordance with this disclosure.

Figure 12:
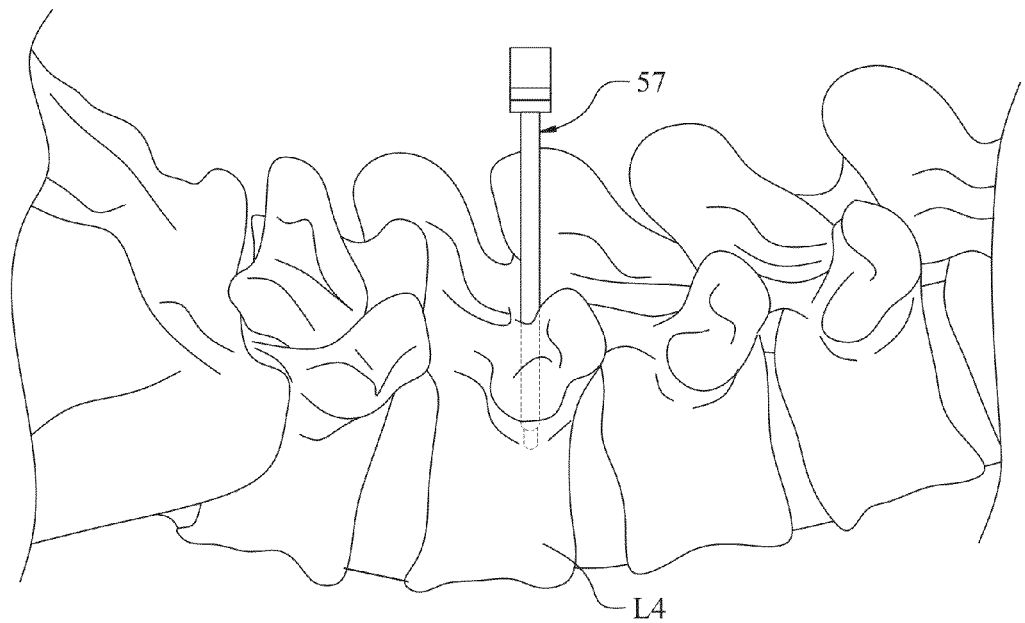
FIGS. 12-26 illustrate surgical techniques or methods of the present disclosure utilizing a cannulated fenestrated pedicle screw of the present disclosure in a minimally invasive surgical (MIS) procedure. More particularly.
Figure 13:
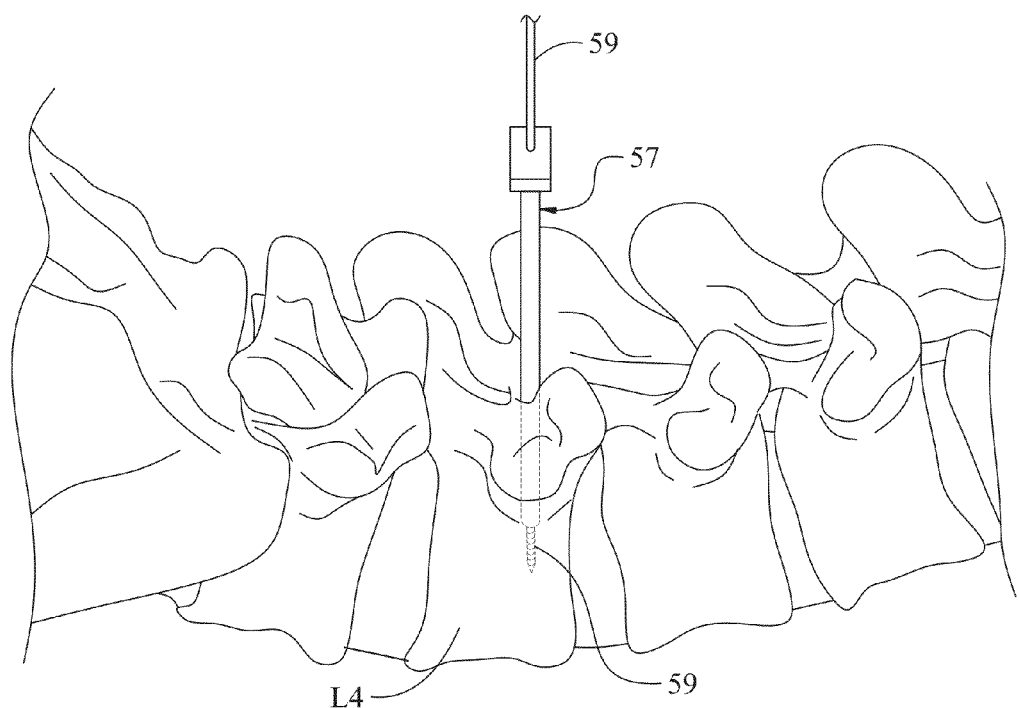
Figure 14:
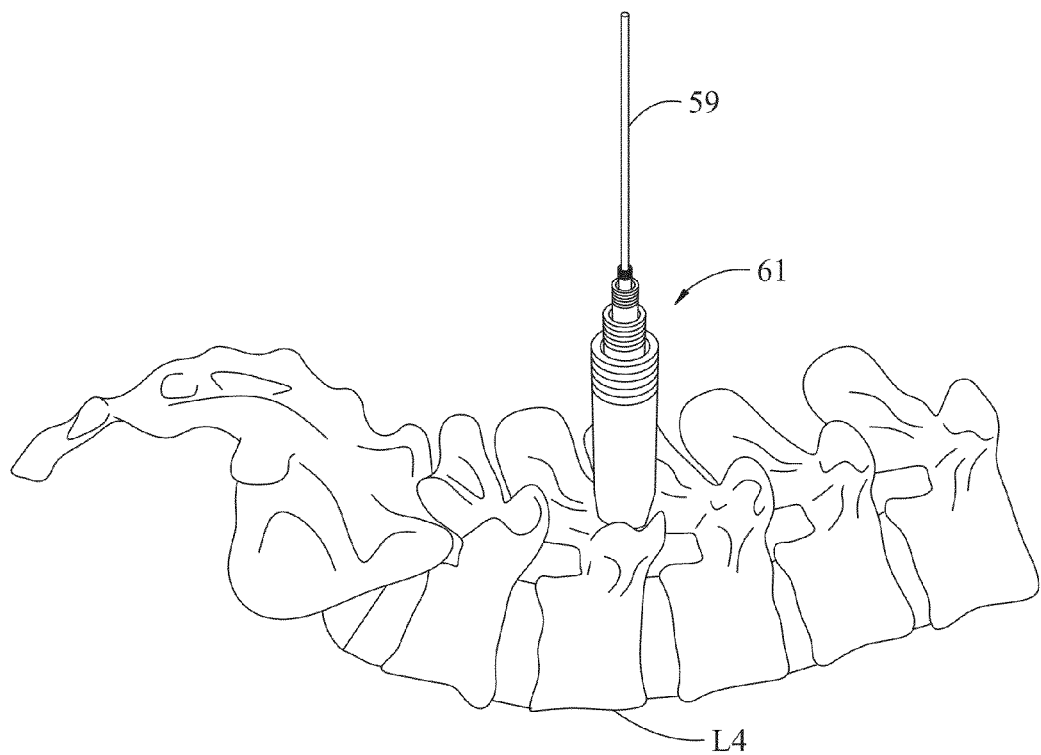
Figure 15:
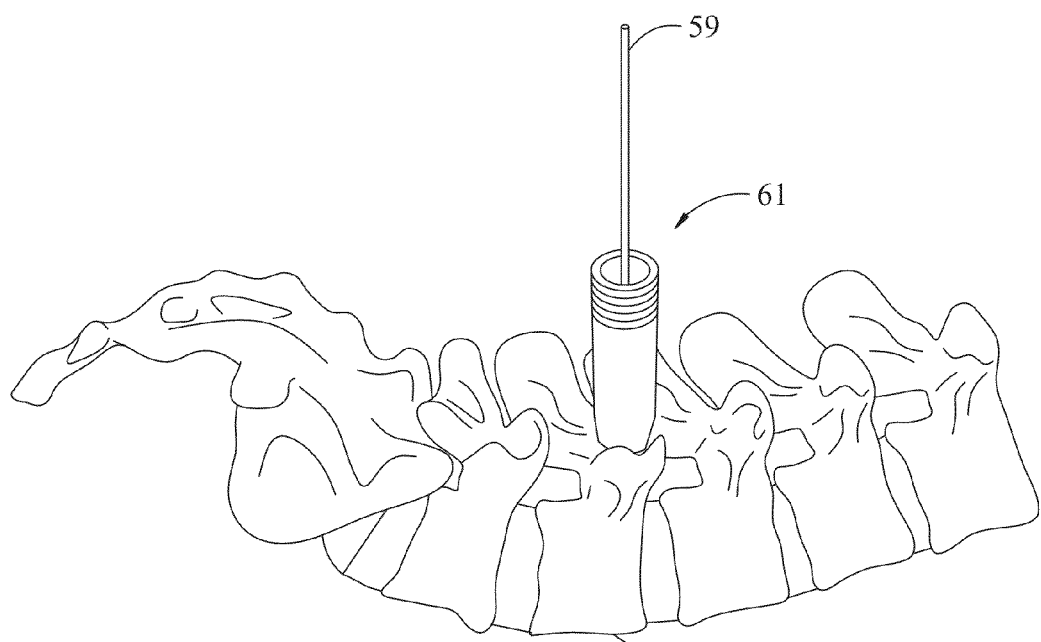

Referring now to FIGS. 12-26, a procedure or surgical method for minimally invasive surgery (MIS) utilizing the cannulated, fenestrated pedicle bone screws 1 or 1' for the injection of bone cement into the bone structure surrounding the screw of the present disclosure is illustrated. As shown in FIG. 12, after a posterior percutaneous incision is made proximate the desired location of where the bone screw 1 to be installed, a Jamshidi needle and trocar 57 is inserted into the incision until it contacts the desired bone structure, for example a pedicle of lumbar vertebrae L4, and is forced into the vertebrae. This is preferably done under fluoroscopic visualization to insure proper location of the trocar and the subsequent location for insertion to screw 1 or 1' into the vertebrae. As shown in FIG. 13, a sharp guide wire 59 is inserted through the Jamshidi needle into the bone structure of the vertebrae in the conventional manner. As shown in FIG. 14, sequential dilation tubes, as generally indicated at 61, are installed over the guide wire 59 in the conventional manner so as to adequately dilate the fascia and muscle surrounding the incision thereby to provide a MIS surgical corridor. As shown in FIG. 15, the smaller diameter dilation tubes 61 are removed and the largest diameter tube remains in place to create the surgical corridor.

Figure 16:
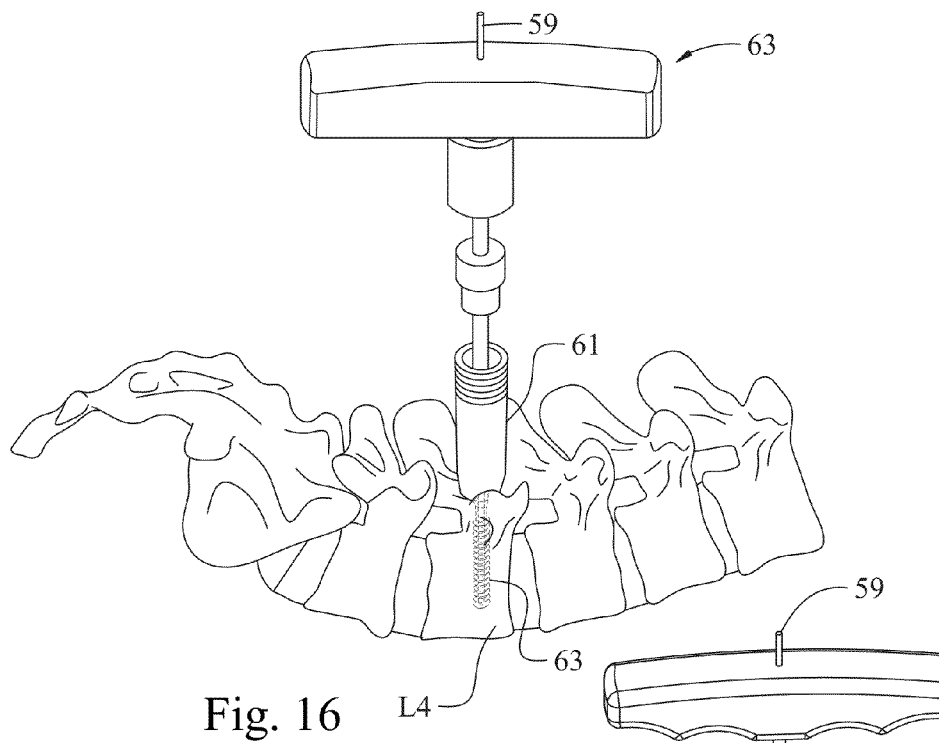
Figure 17:
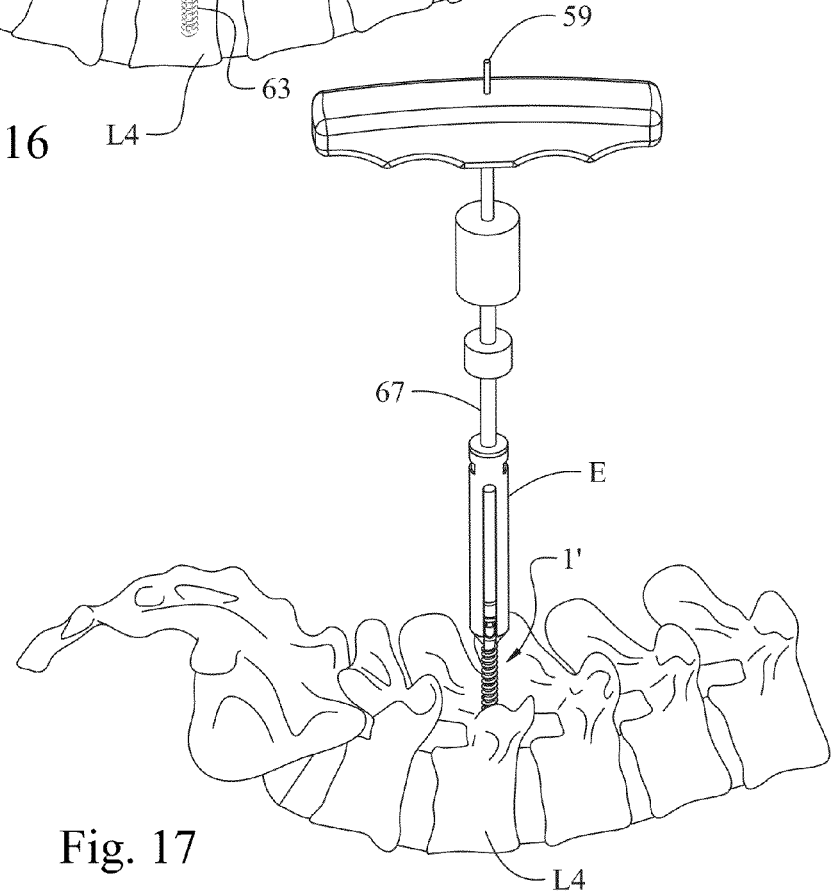

As shown in FIG. 16, a pilot hole is created in the vertebrae with a cannulated tap 63 inserted through dilator tube 61 passed over the guide wire 59. In FIG. 16, the smaller diameter dilator tubes 61 (as shown in FIG. 14) have been removed. A screw extender, as generally indicated at E in FIG. 17, as is conventionally used in minimally invasive spine surgery, allows mechanical connection and continuity with the pedicle screw which will be deep in the soft tissues and which is not visible to the surgeon. The extender E protrudes through the wound and allows the surgeon to manipulate or drive the screw. It has a central working channel through which a cannulated screw driver 67 can be passed through and rod placement is permitted. The extender is attached to screw 1 or 1' and a cannulated screw driver is passed down the central working channel of the extender is used to advance the screw 1' over a guide wire 59. Screw 1' is advanced nearly to the end of the guide wire but not to the end so as to prevent binding of the wire to the screw or shearing of the wire. Such screw extenders are known and one such example is disclosed in the Sextant system commercially available from Medtronic Sofamor Danek, and as is disclosed at www.mtortho.com/public/CD_HORIZON_sextantII_st.pdf, which is herein incorporated in its entirety by reference.

Figure 18:
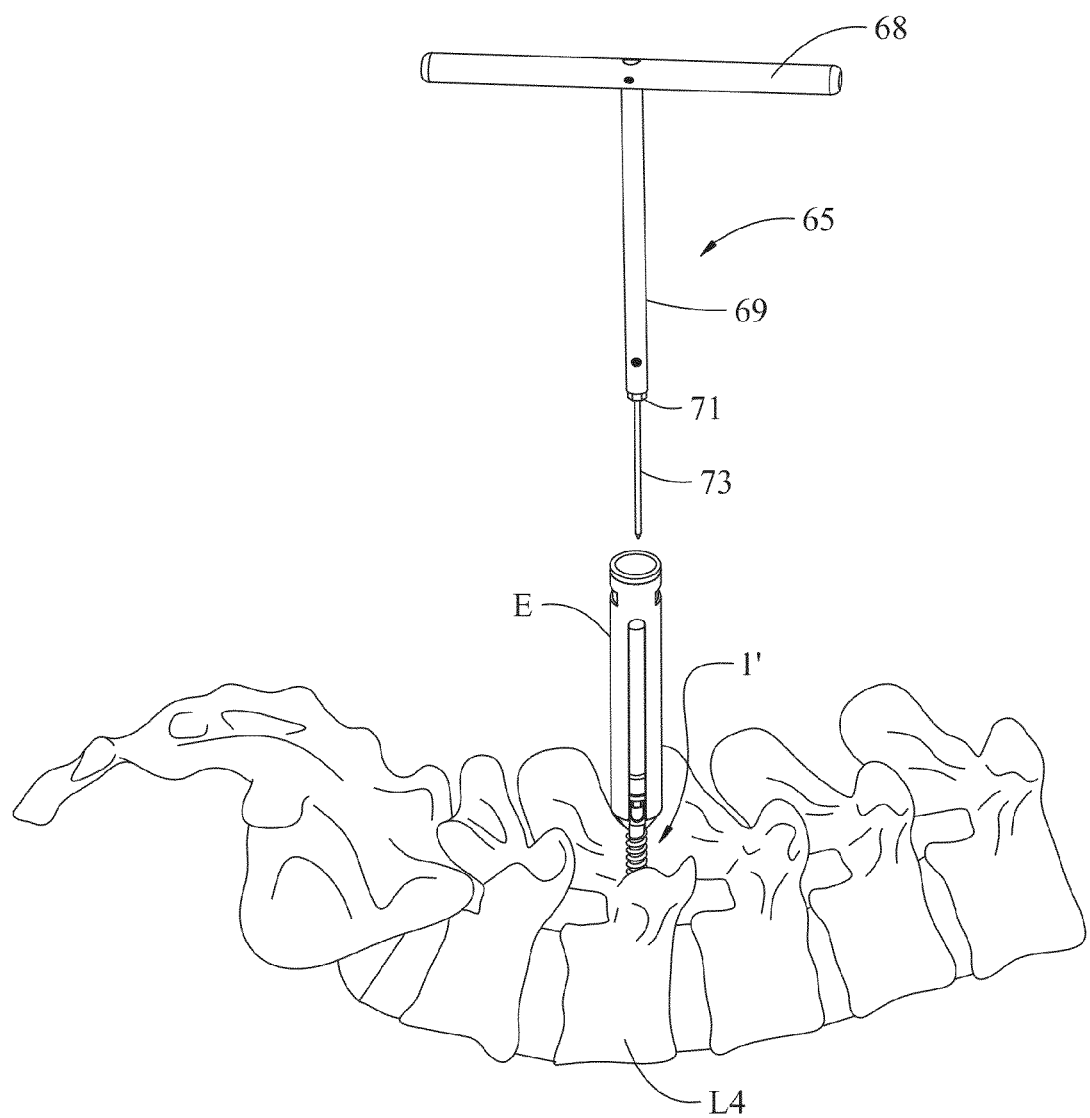

As shown in FIG. 18, the guide wire 59 has been withdrawn and a screwdriver 65 of the present disclosure having a rod extension 73 is employed to advance (drive) screw 1' into the anterior one third of the vertebral body. Screw driver 65 has a T handle 68 and a shaft 69. The outer end of the shaft has a male screw driver head 71 thereon that is adapted to mate with the female socket 21 in screw 1 or 1'. For example, screw driver head 71 may have a male hex driver that is received within the hex-shaped female drive socket 21 in the screw 1 or 1'. As shown in FIG. 18, extension rod 73 extends from driver head 71 and is received in the cannula 7 of the screw. This extension rod 73 is preferably sized to have a diameter just slightly smaller than the diameter of the cannula 7 of the screw 1' and is of such a length such that with screw driver head 71 received in drive socket 21 of the screw, the extension rod extends nearly the full length of the cannula 7 and stops at or just short of the blind end of a blind cannulated screw 1, or it stops just short of tip 9 of a fully cannulated screw 1'. In this manner, with the extension rod received in cannula 7, the extension rod prevents a bone core or other debris from entering the cannula upon advancing a fully cannulated screw 1' where such bone core may occlude or block the cannula 7. For either a blind end screw 1 or a fully cannulated screw 1', the extension rod also prevents bone debris from entering cannula 7 via the side bores or fenestrations 11 as the bone screw is advanced into the bone structure. Thus, the surgeon can advance the screw 1 to its desired final installed position with central cannula 7 of the screw effectively protected against occlusion by bone material. To the extent that any bone debris occludes the fenestrations, the pressure of the bone cement upon operating pump 41 is sufficient to overcome such debris in the fenestrations so that the bone cement may be injected into the bone structure adjacent the fenestrations.

Figure 19:
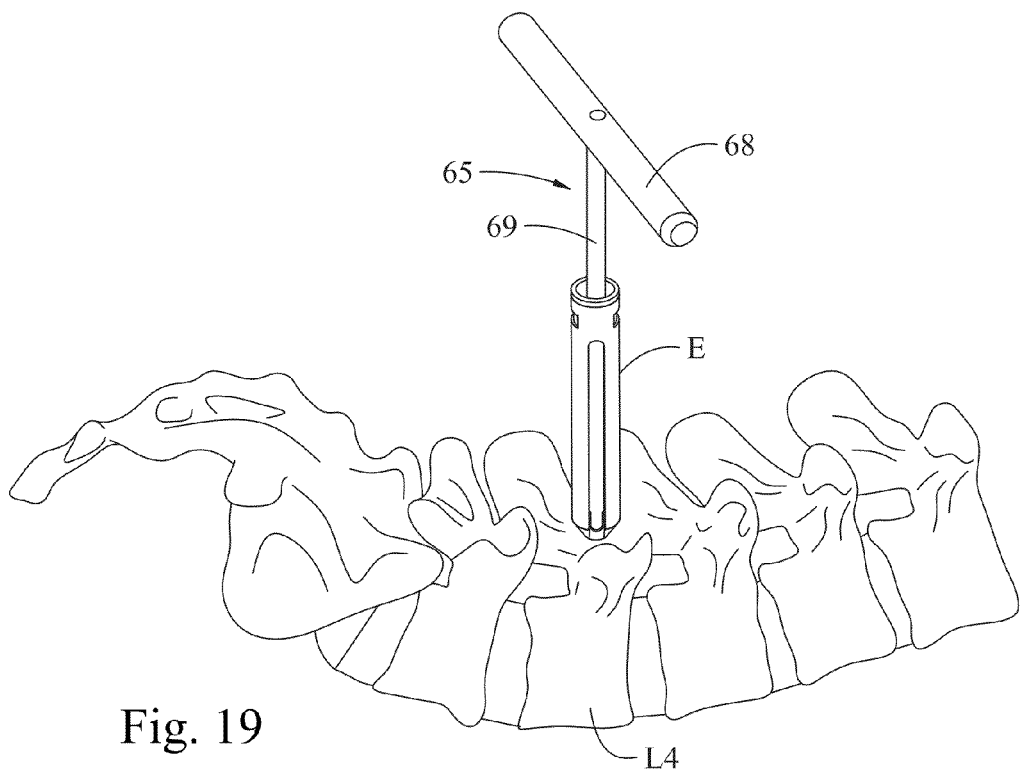
Figure 20:
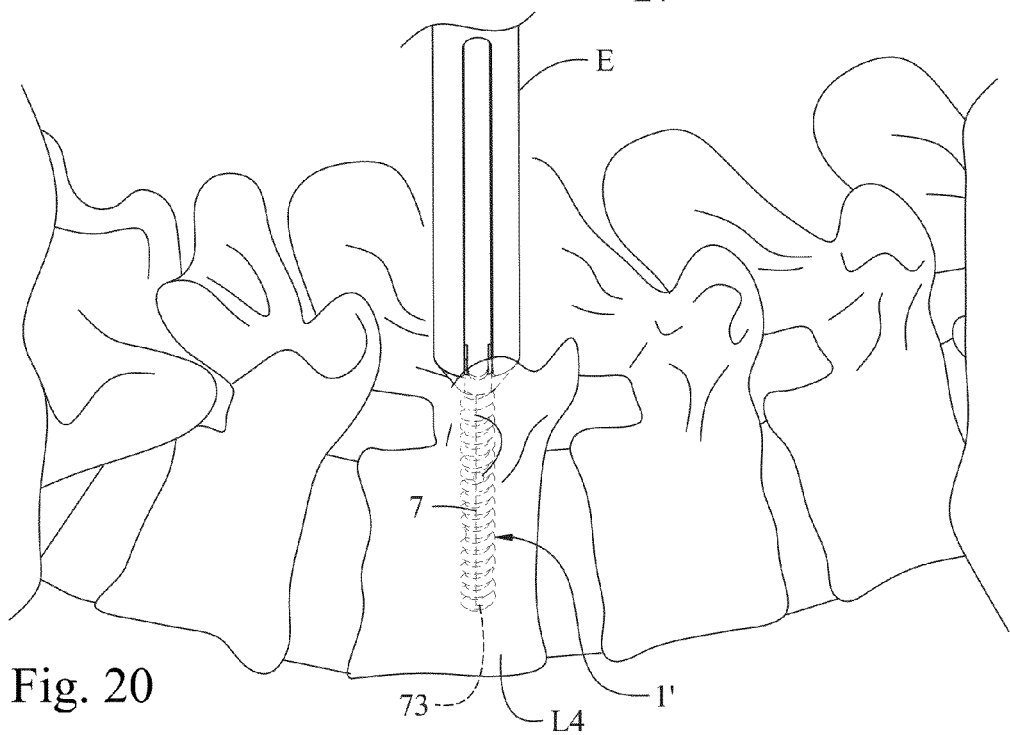

FIG. 19 further illustrates the final positioning of a fenestrated screw 1 or 1' using the screw driver 65 having an extension rod 73. FIG. 20 is an enlarged view of FIG. 19 showing the final desired position of the fenestrated screw 1' (as shown in dotted lines) in the vertebral body.

Figure 21:
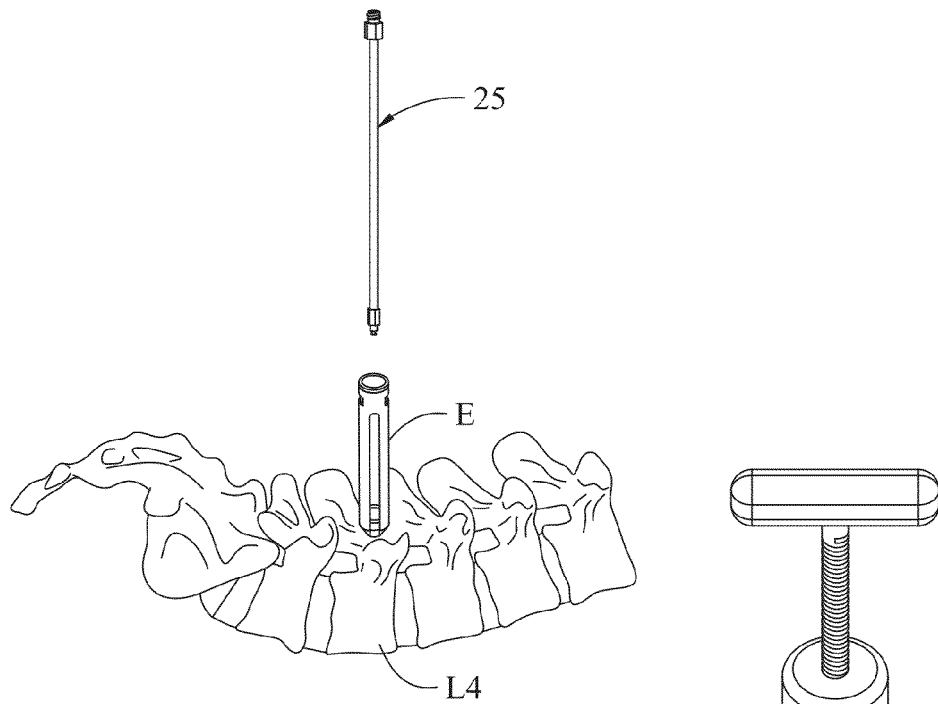
Figure 22:
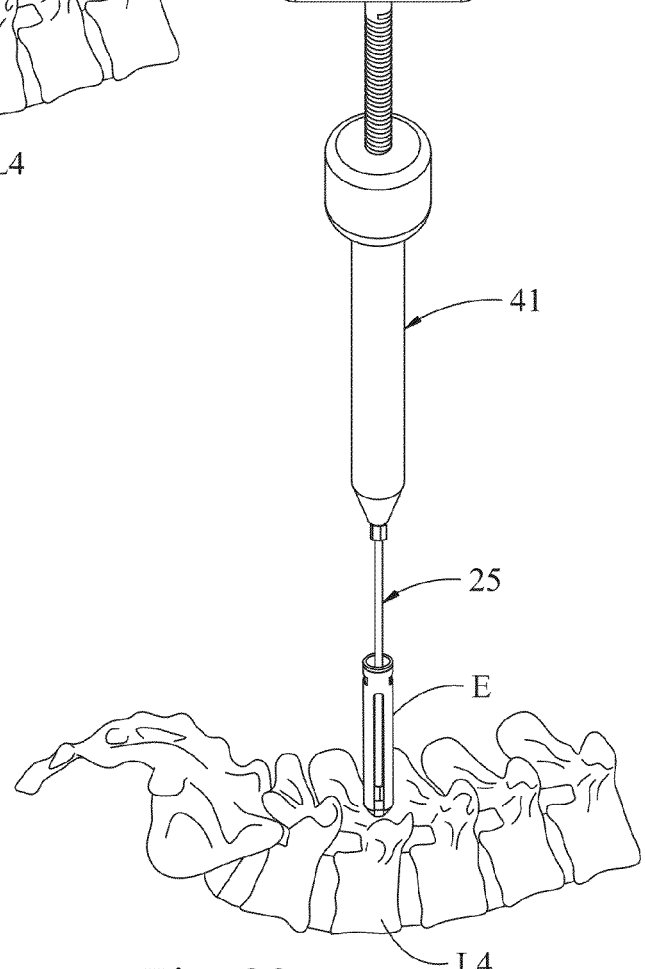

FIG. 21 illustrates a cement delivery tube 25 about to be connected to the head H of a fenestrated pedicle screw in the manner heretofore described. Referring to FIG. 22, the attachment of the cement injecting tube 25 to the screw 1' of the present disclosure is illustrated in the manner heretofore described. As previously described, a flexible hose (not shown) may be used to connect pump 41 to tube 25.

Figure 23:
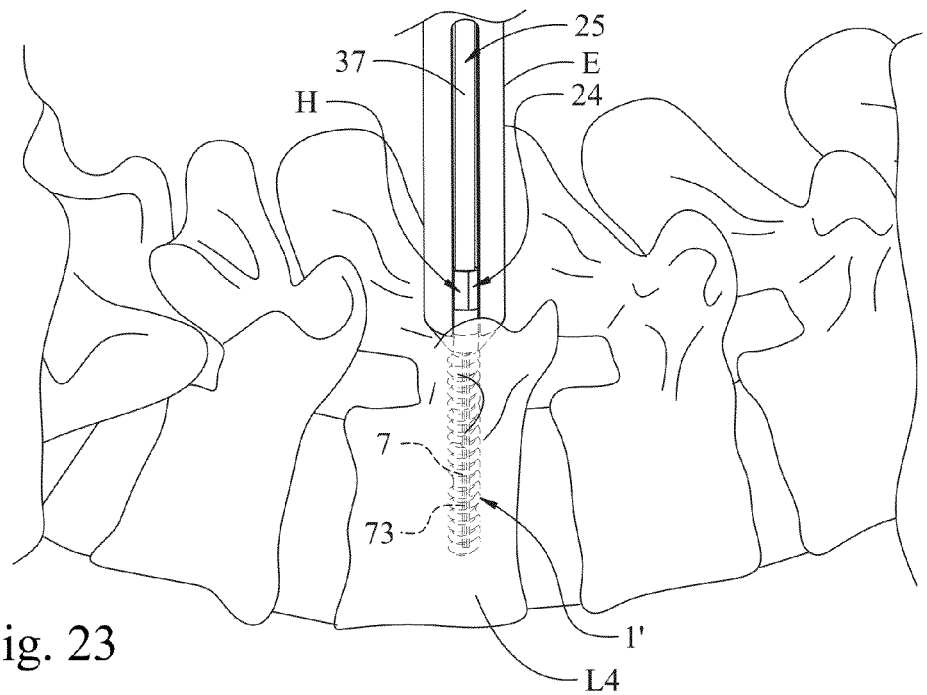
Figure 24:
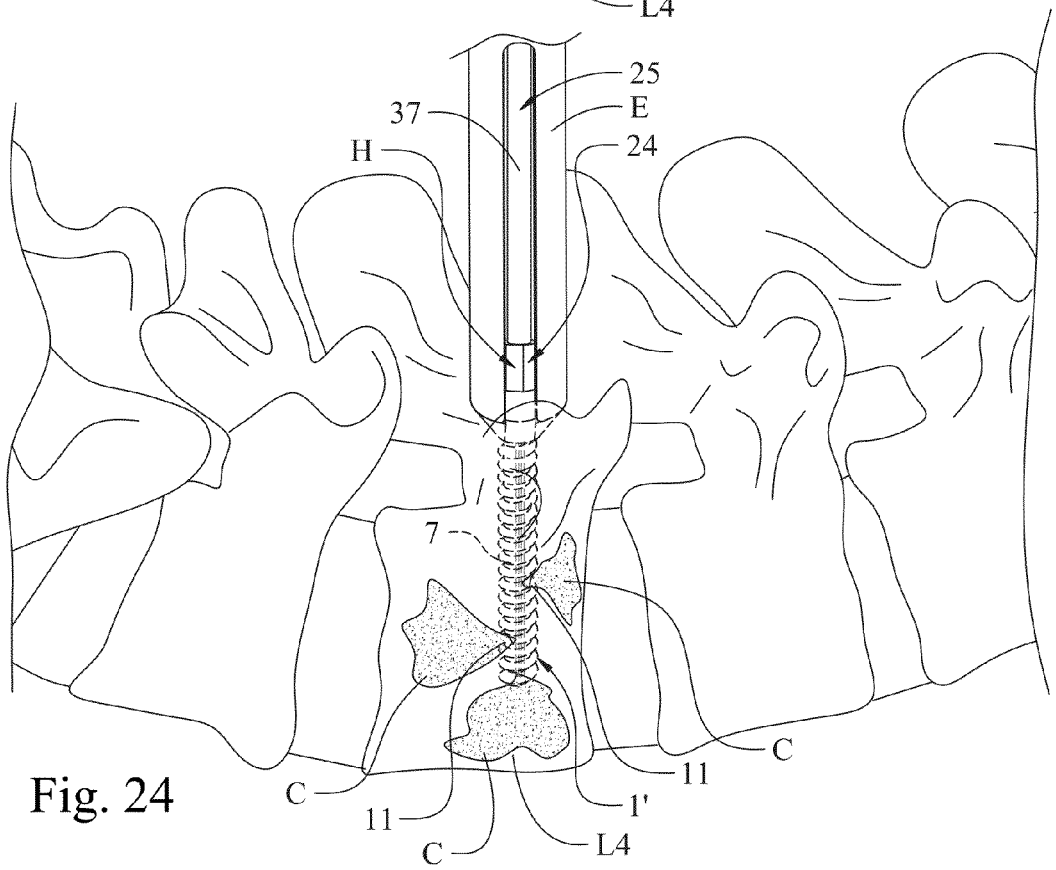

With the tube 25 so attached to the screw 1', the surgeon attaches cement pump 41 to connector 39 on tube 25. Of course, the cement pump will contain a supply of pre-mixed bone cement C, such as PMMA or other suitable bone cement. It will also be apparent that, any one of a number of known cement pumps other than pump 41 heretofore described may be used in accordance with the instant disclosure. FIG. 23 illustrates on enlarged scale the connection of the cement delivery tube to the head of a bone screw in accordance with the present disclosure.

As bone cement is pumped under pressure from pump 41 into the cannula 7 of screw 1 or 1', the cement will flow lengthwise of the screw and will be forced from fenestrations 11 and from the tip of a fully cannulated screw 1' and injected into the surrounding bone structure. The cement injected into the surrounding bone structure is indicated at C in FIGS. 24 and 25.

Figure 26:
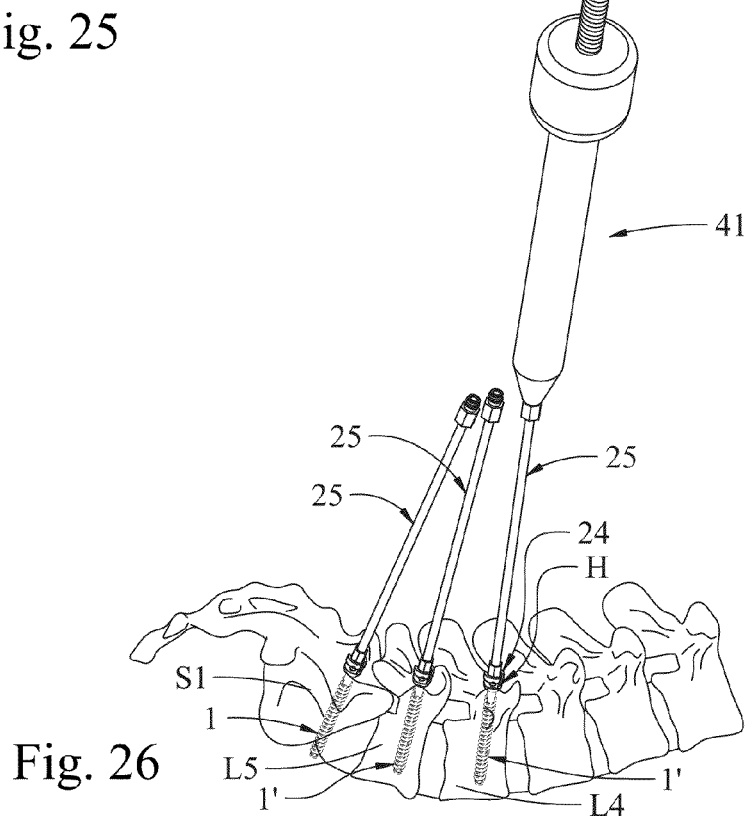

FIG. 26 illustrates an open surgical procedure of the present disclosure for multi-level fixation where either blind or fully cannulated bone screws 1 or 1' of the present disclosure are installed in respective adjacent vertebrae, and where each screw has a respective tube 25 attached to each of the bone screws in the manner as above describe. A cement pump 41 may be readily connected to a first screw 1, and cement may be injected through the fenestrated screw into the bone structure proximate the first screw. As previously described, bone cement C is preferably a radio opaque cement and the injection of bone cement is done under fluoroscopic viewing. When the surgeon observes that a sufficient amount of bone cement has been injected into the bone structure surrounding the screw 1 or 1', then, in accordance with the present disclosure, the cement pump 41 may be readily uncoupled from the first screw and coupled to the next screw in the same manner as above described. Bone cement is then injected into the bone structure proximate the second screw. This process may be repeated until all of the bone screws have bone cement injected into the bone structure surrounding that screw.

Figure 25:
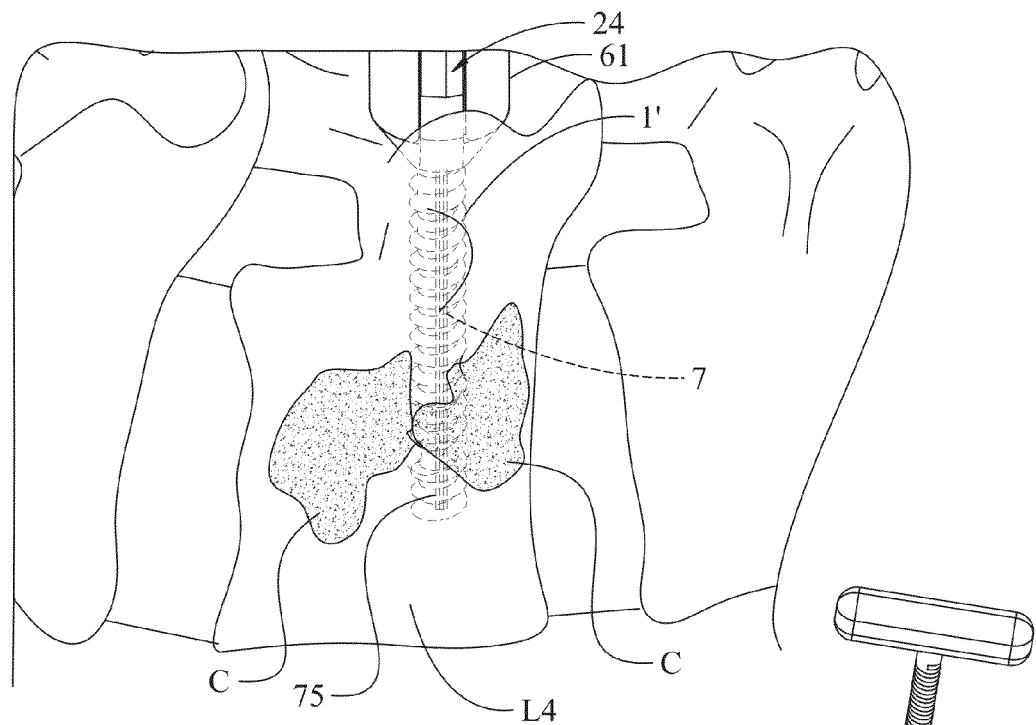

Still further in accordance with the present disclosure, prior to disconnection of tube 25 from the head of screw 1 or 1', pump 41 is disconnected from tube 23 and a plunger 75, as shown in FIG. 25, may be inserted through tube 25 into the cannula 7 of the bone screw clearing residual cement from the central bore of the bone screw. It will be understood that the plunger 75 is rod sized to have a diameter slightly less than the diameter of cannula 7 so that as the plunger is inserted into the cannula, the plunger forces a portion of the cement in the cannula out through the fenestrations, or in the case of a fully cannulated screw 1, out through the fenestrations and the open tip of the screw. This, in turn, prevents backpressure from causing the leakage of cement proximally through cannula 7 into the saddle of the polyaxial screw interfering with rod placement upon removal of the tube 25 from the screw.

It will be appreciated that because tube 25 is positively and sealably connected to the bone screw 1 or 1', the bone cement may be injected into the bone structure with considerable pressure and yet the cement will not leak from the connection of the tube 25 to the screw. Thus, the injected bone cement not only reinforces the bone structure and increases pedicle screw pullout strength, but larger volumes of cement may be injected at the surgeon's discretion so as to result in the performance of de novo vertebroplasty that mechanically stabilizes the vertebrae and strengthens the soft inner bone structure of the vertebrae, especially osteoporotic bone.

Referring now to FIG. 26, this illustrates an open surgical technique (as opposed to a MIS technique), in which a plurality of screws 1 or 1' are installed on a plurality of adjacent vertebrae (e.g., L4-S1), and where each screw has a cement delivery tube 25 attached thereto in the manner as above described. A cement pump 41 is attached to the first of the screws (as shown) and the surgeon injects a desired amount of cement into the bone structure proximate the fenestrations 11 of the first screw in the manner heretofore described. The surgeon then disconnects the pump from the first tube 25 and inserts the plunger 75 through tube 25 and through much of the cannula 7 of screw 1 or 1' to clear the cannula of cement so that when the tube 25 is disconnected from the screw, excess cement does not leak when the connection between the tube and the screw is broken for removal of the tube from its respective screw. Then, after the plunger has been used, the surgeon removes the tube from the screw in the manner heretofore described. The surgeon then connects the cement pump to the next tube 25 and repeats the above-described procedure until all of the screws 1 or 1' have had bone cement injected into their respective proximate bone structures. This technique allows the surgeon to quickly perform the injection of cement into a plurality of screws, while minimizing the chances of leakage of cement into the wound site.

Figure 27A:
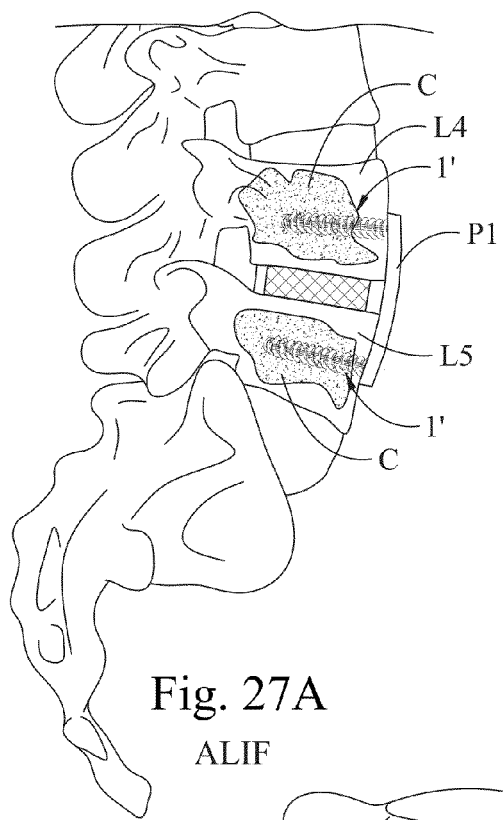
FIGS. 27A-27C illustrate the use of fenestrated bone screws of the present disclosure and surgical techniques of the present disclosure in conjunction with known spine surgeries to prevent interbody implant subsidence.

FIG. 27A is a view of the lower spine illustrating the placement of screws 1 of the present disclosure installed in two adjacent vertebrae bodies to be fused (e.g., L5 and L4) to secure an ALIF plate P1 that spans between the adjacent vertebrae bodies. The screws permit the injection of bone cement into the bone structure adjacent the screws in anterior lumbar interbody fusion (ALIF) surgery. Traditional ALIF screws are solid, while in FIG. 27A these traditional screws have been replaced with blind end cannulated screws 1 of the present disclosure having the bayoneted coupling mechanism of this disclosure to permit cement injection. The head H of the screw 1 is modified to be compatible with anterior lumbar plate P1.

Figure 27B:
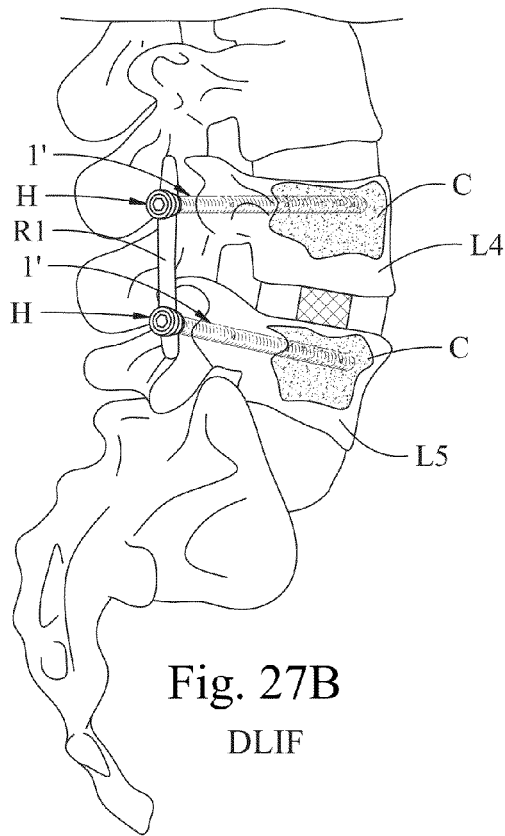

FIG. 27B is a similar view of the lower spine illustrating the placement of screws 1' of the present disclosure installed in lumbar vertebrae L5 and L4 and the injection of bone cement into the bone structure adjacent the screws in direct lateral interbody fusion (DLIF) surgery. Screws secure a rod R1 which spans between the vertebrae bodies (e.g., L4, L5) to be fused by DLIF surgery and rigidly connects screws 1'.

Figure 27C:
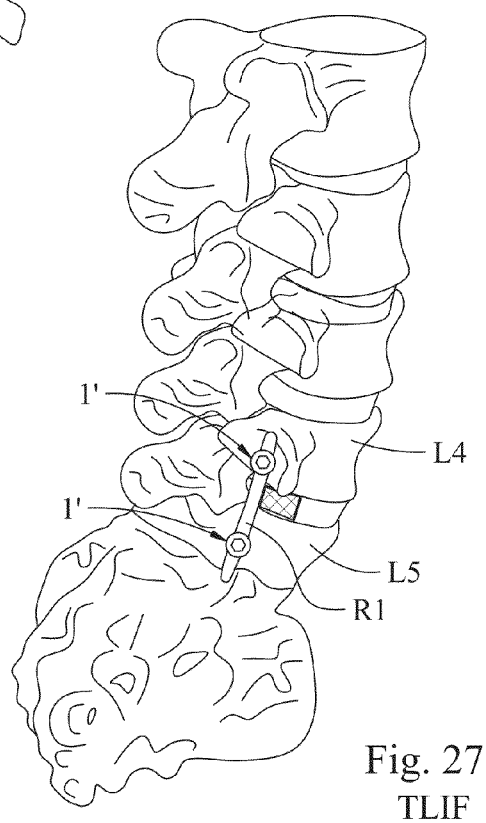

FIG. 27C is a view of the lower spine illustrating the placement of screws 1' installed in lumbar vertebrae L5 and L4 and the injection of bone cement into the bone structure adjacent the screws in transforaminal lateral interbody fusion (TLIF) surgery. Again, screws secure a R1, which spans between the vertebrae bodies (e.g., L4, L5) to be fused. In all three techniques, i.e., ALIF, DLIF, and TLIF, larger volumes of cement injection would result in vertebral body augmentation, i.e., vertebroplasty. This mechanically strengthens the vertebral body and minimizes the chance of interbody implant subsidence as well as increasing screw pullout strength.

As various changes could be made in the above constructions without departing from the broad scope of the invention, it is intended that all matter contained in the above description or shown in the accompanying drawings shall be interpreted as illustrative and not in a limiting sense.

The invention claimed is:

1. A bone screw having a shank, a tip, and a head, at least a portion of said shank having threads thereon configured to be threaded into bone structure, said shank having a longitudinal cannula therein, at least one fenestration extending outwardly from said cannula to the exterior of said screw, a central opening in the outer end of the head configured to form a socket for receiving a driving tool for driving the screw into bone structure, said opening having a first connector inwardly of said socket and being adapted to be connected to a source of bone cement so that bone cement may be delivered to said cannula of said screw and forced out of said at least one fenestration and into bone structure proximate said at least one fenestration, said source of bone cement comprising a cement injection tube adapted to be connected to a suitable bone cement pump, said cement injection tube carrying a second connector adapted to be coupled to said first connector for the delivery of bone cement into said cannula of said bone screw, wherein one of said connectors is a male connector and the other of said connectors is a female connector, said female connector having an opening adapted to receive at least a portion of said male connector and having at least one connection slot comprising an axial slot and a circumferential slot, wherein said male connector has at least one tang configured to be received in a respective connection slot in said female connector so that upon said tang being aligned with the axial slot of its respective connection slot in said female connector and upon said tube being moved axially toward said screw, said tang moves along said axial slot in said female connector until the tang is in register with said circumferential slot whereupon upon rotation of said tube in one direction moves said tang into said circumferential slot thereby to secure said tube to said screw.

2. A bone screw as set forth in claim 1 wherein said cannula stops short of the distal end of the screw such that the screw is a blind end cannulated screw.

3. A bone screw as set forth in claim 1 wherein said cannula extends through the tip of the bone screw so that upon said injection of said cement into said cannula, said cement is forced out of the end of the cannula and into bone structure proximate the tip of the screw.

4. A bone screw as set forth in claim 1 wherein said threads each have a crest and a root, and wherein the outer end of said at least one of said fenestration is substantially centered on a thread crest.

5. A bone screw as set forth in claim 4 wherein said thread crest upon which said at least one fenestration is substantially centered has one edge constituting a leading edge and another edge constituting a trailing edge such that upon rotation of said screw into said bone structure said leading and trailing edges minimize the entry of bone material into said fenestration.

6. A bone screw as set forth in claim 1 wherein said first connector is said female connector and said second connector is said male connector.

7. A bone screw as set forth in claim 1 wherein said female connector has a pair of said connection slots and wherein said male connector has a pair of said tangs with each of said tangs being configured to be received in a respective one said connection slots.

8. A bone screw as set forth in claim 7 wherein each of said circumferential slots has a blind end and a detent proximate said blind end configured to receive a respective tang such that upon rotating said tube in said one direction said tube and said male connector are releasably secured to said connector with said seal being at least partially compressed such that the seal resiliently maintains said male connector and said connector in a mechanically coupled, sealed relation.

9. A bone screw as set forth in claim 8 wherein the end of each said detent toward its respective said axial slot has a sloped cam surface thereon, such that when it is desired to uncouple said tube from said screw, said tube is rotated in the opposite direction thus causing said tangs to encounter their respective said sloped cam surfaces thereby to guide each said tang into its respective said circumferential slot.

10. A bone screw as set forth in claim 9 whereupon further rotation of said tube in said opposite direction causes said tangs to move through said circumferential slots into register with said axial slots at which point said tube may be removed from said screw.

11. A bone screw as set forth in claim 1 further comprising a seal configured to be disposed between said male connector and said connector so that when said tangs are received within said circumferential slots said cement injection tube is sealably connected to said screw.

12. A bone screw as set forth in claim 11 wherein said seal is an O-ring.

13. A bone screw as set forth in claim 11 wherein said seal is carried by said male connector.

14. A bone screw having a shank, a tip, and a head, at least a portion of said shank having threads thereon configured to be threaded into bone structure, said shank having a central longitudinal cannula, one or more fenestrations extending outwardly from said cannula to the exterior of said screw, a central opening in the outer end of said head in communication with said cannula and being configured to form a socket for receiving a driving tool for driving the screw into bone structure, said opening having a female connector within said head inwardly of said socket configured to receive a male connector, the latter being adapted when in communication with a source of bone cement to deliver bone cement to said cannula and to introduce bone cement into said bone structure adjacent said one or more fenestrations when said bone screw is threaded into said bone structure, said female connector having a central opening therethrough adapted to receive said male connector and having a pair of axial slots with each of said axial slots having a circumferential slot extending in a first circumferential direction from its said axial slot, said male connector having a hub on its distal end, a pair of tangs extending outwardly from said hub with each said tang being adapted to be received in a respective said axial slot of said female connector when said hub is received in said central opening of said female connector so that said male connector may move axially with respect to said screw until said tangs are in register with said circumferential slots at which point said male connector may be rotated relative to said screw such that said tangs move into said circumferential slots to thereby sealably connect said male connector to said screw.

15. A bone screw as set forth in claim 14 further comprising a seal between said male connector and said connector.

16. A bone screw as set forth in claim 15 wherein said seal is an O-ring.

17. A bone screw as set forth in claim 14 wherein said male connector is carried on a cement delivery tube with the latter being adapted to be connected to a bone cement pump for delivery of bone cement to said cannula of said screw and to be injected into said bone structure adjacent said fenestrations.

\* \* \* \* \*